US011285022B2

(12) United States Patent
Marrapode et al.

(10) Patent No.: US 11,285,022 B2
(45) Date of Patent: Mar. 29, 2022

(54) SPINAL IMPLANT SYSTEM AND METHOD

(71) Applicant: Warsaw Orthopedic, Inc., Warsaw, IN (US)

(72) Inventors: Matthew T. Marrapode, Boulder, CO (US); Julien J. Prevost, Memphis, TN (US); Fuad N. Mefleh, Thornton, CO (US); Shelley B. Szalay, Broomfield, CO (US); Jerald L. Redmond, Germantown, TN (US); Nikita Pandey, Superior, CO (US); Eric A. Potts, Indianapolis, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 303 days.

(21) Appl. No.: 16/383,760

(22) Filed: Apr. 15, 2019

(65) Prior Publication Data

US 2020/0323654 A1 Oct. 15, 2020

(51) Int. Cl.
| | | |
|---|---|---|
| *A61F 2/46* | (2006.01) | |
| *A61F 2/44* | (2006.01) | |
| *A61B 90/00* | (2016.01) | |
| *A61B 34/20* | (2016.01) | |

(52) U.S. Cl.
CPC ............ *A61F 2/4684* (2013.01); *A61B 34/20* (2016.02); *A61B 90/39* (2016.02); *A61F 2/4455* (2013.01); *A61F 2/4611* (2013.01); *A61B 2034/2072* (2016.02); *A61B 2090/3916* (2016.02); *A61B 2090/3983* (2016.02)

(58) Field of Classification Search
CPC ............ A61B 90/39; A61B 2090/3904; A61B 2090/3916; A61B 2090/3983; A61B 2090/3991; A61B 17/1659; A61B 17/1662; A61B 17/1671; A61F 2/4455; A61F 2/4611; A61F 2/4684
See application file for complete search history.

(56) References Cited

U.S. PATENT DOCUMENTS

| | | | | |
|---|---|---|---|---|
| 5,250,061 A * | 10/1993 | Michelson | ......... | A61B 17/1671 606/160 |
| 5,395,372 A * | 3/1995 | Holt | ................... | A61B 17/7059 606/75 |
| 5,993,204 A * | 11/1999 | Stubbs | ..................... | A61D 5/00 433/1 |
| 6,348,058 B1 * | 2/2002 | Melkent | ............ | A61B 17/1757 600/429 |

(Continued)

OTHER PUBLICATIONS

International Search Report and Written Opinion of the International Searching Authority—PCT/US2019/056876—dated Feb. 6, 2020, the ISA/KR-International Application Division—Korean Intellectual Property Office, 189 Cheongsa-ro. Seo-gu, Daejeon, 35208, Republic of Korea.

*Primary Examiner* — Anu Ramana
(74) *Attorney, Agent, or Firm* — Sorell, Lenna & Schmidt, LLP

(57) ABSTRACT

A spinal implant template includes a shaft extending along an axis between a proximal end and a distal end. An engagement portion is configured for insertion between vertebrae of a patient. The engagement portion includes a rod extending from the distal end at an acute angle relative to the longitudinal axis to facilitate ease of entry around a spinal cord of the patient. Systems, surgical instruments, spinal implants and methods are disclosed.

15 Claims, 16 Drawing Sheets

(56) References Cited

U.S. PATENT DOCUMENTS

| | | | | |
|---|---|---|---|---|
| 6,764,491 | B2* | 7/2004 | Frey | A61B 17/1642 606/85 |
| 7,063,705 | B2* | 6/2006 | Young | A61B 90/50 606/86 R |
| 8,123,750 | B2* | 2/2012 | Norton | A61B 17/1631 606/80 |
| 8,366,748 | B2* | 2/2013 | Kleiner | A61B 17/025 606/279 |
| 2005/0038511 | A1* | 2/2005 | Martz | A61B 17/1671 623/17.11 |
| 2007/0260270 | A1 | 11/2007 | Assell | |
| 2008/0243126 | A1 | 10/2008 | Gutierrez | |
| 2009/0306671 | A1* | 12/2009 | McCormack | A61B 17/025 606/90 |
| 2015/0018892 | A1 | 1/2015 | Lindner et al. | |
| 2017/0209286 | A1 | 7/2017 | Palmatier et al. | |
| 2018/0064451 | A1 | 3/2018 | Kleiner | |

* cited by examiner

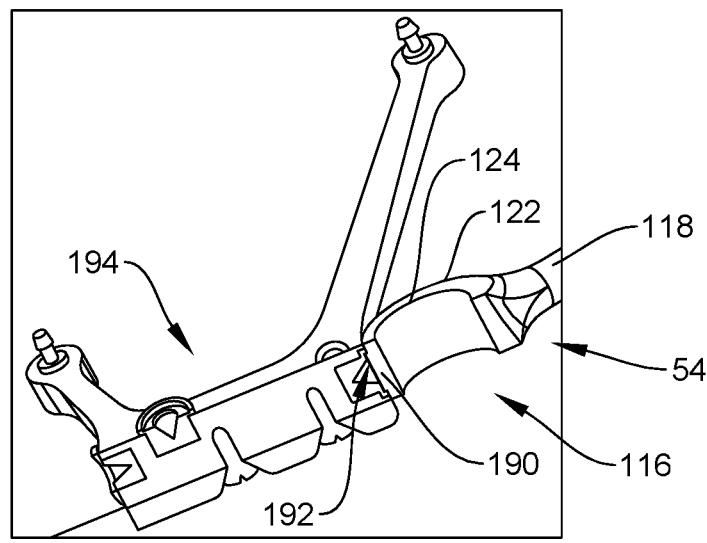
FIG. 14B
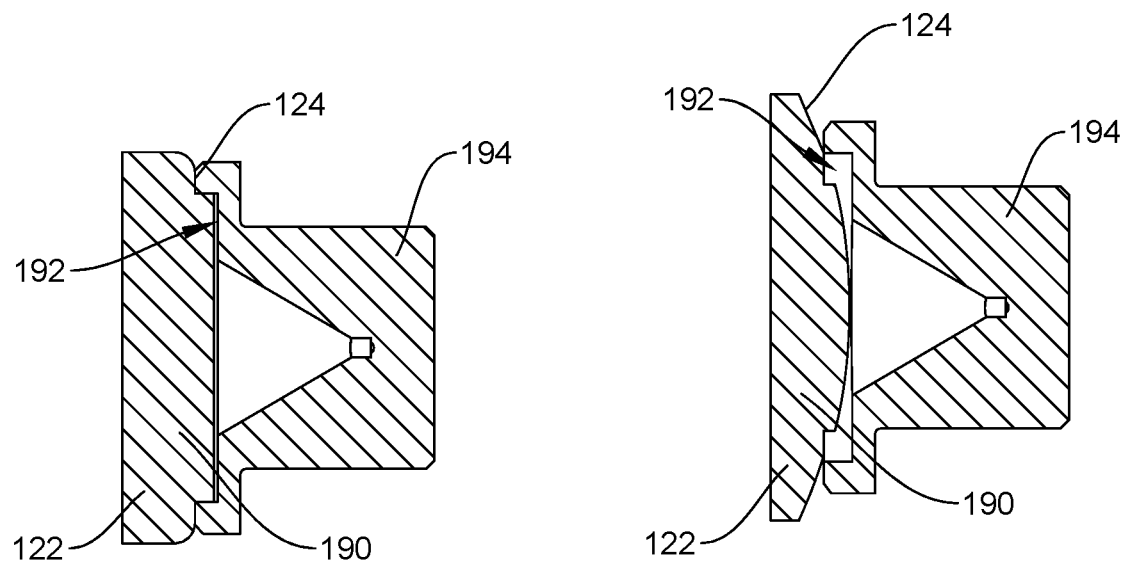
FIG. 15A
FIG. 15B

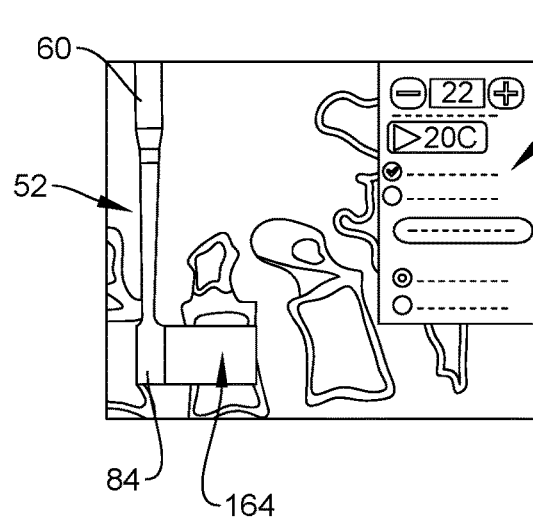 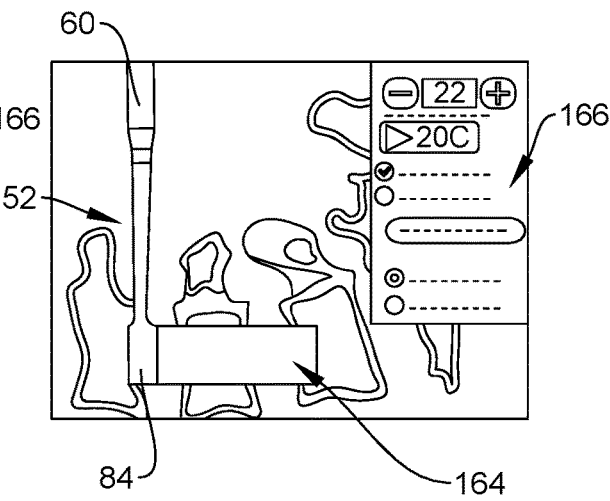
FIG. 20   FIG. 21
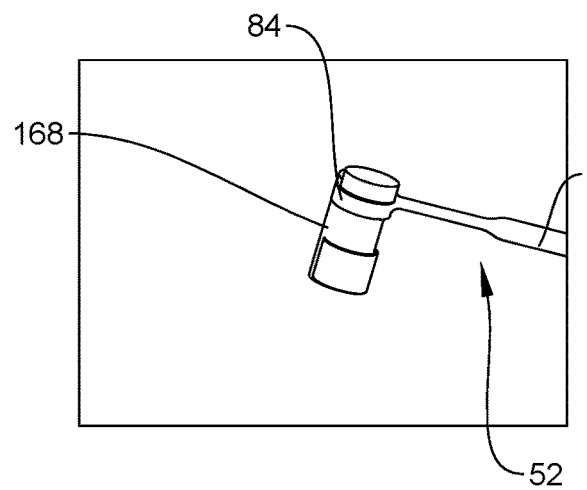 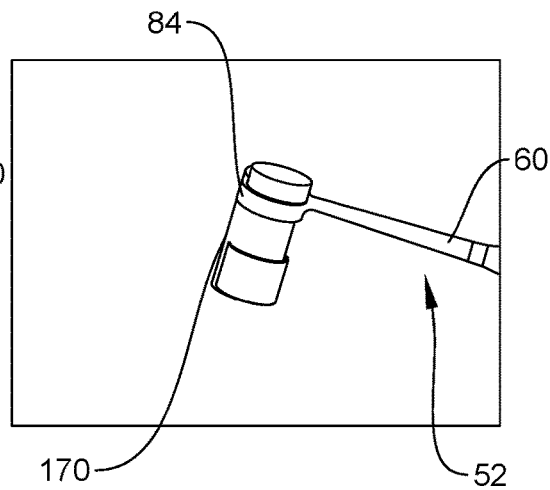
FIG. 22   FIG. 23

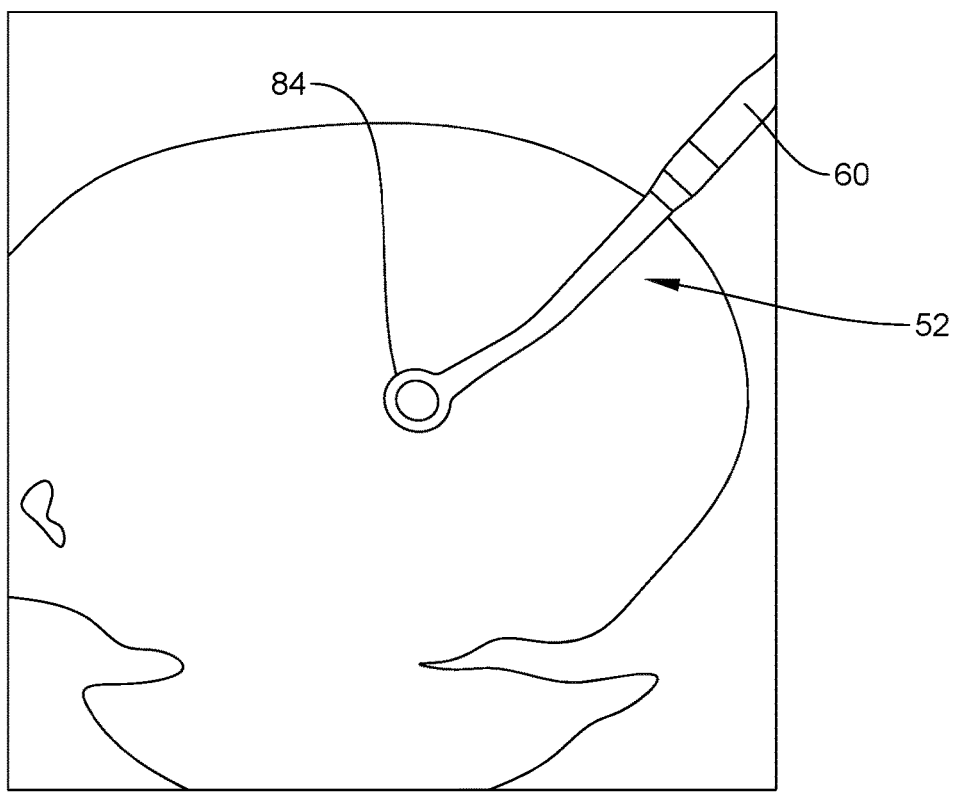
FIG. 24
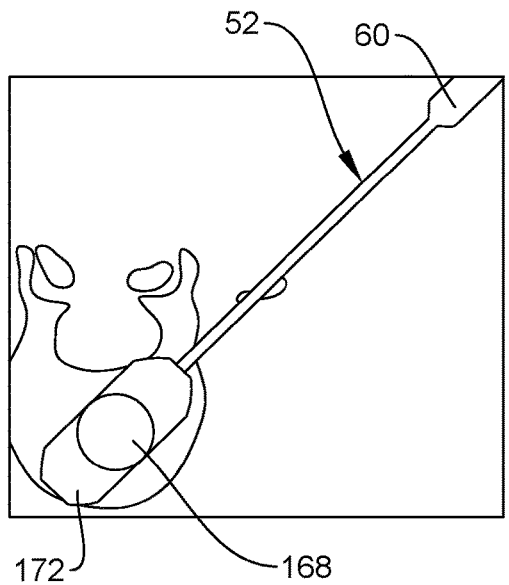 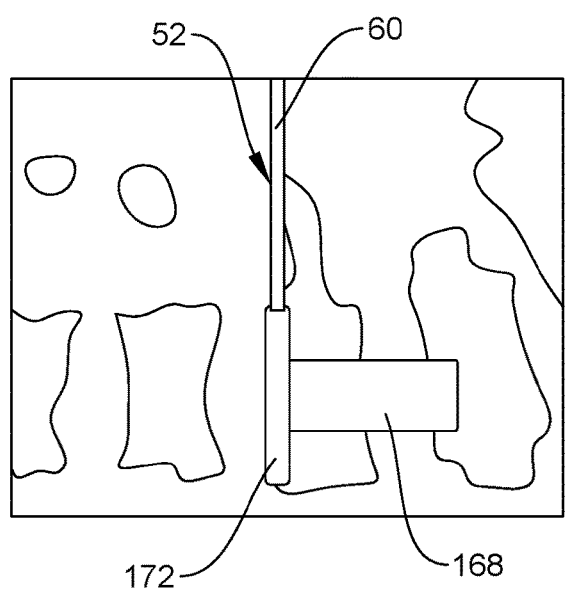
FIG. 25　　　　FIG. 26

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis, kyphosis and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae. This disclosure describes an improvement over these prior art technologies.

SUMMARY

In one embodiment, in accordance with the principles of the present disclosure, a spinal implant template includes a shaft extending along an axis between a proximal end and a distal end. An engagement portion is configured for insertion between vertebrae of a patient. The engagement portion includes a rod extending from the distal end at an acute angle relative to the axis to facilitate ease of entry around a spinal cord of the patient. Systems, surgical instruments, spinal implants and methods are disclosed.

In one embodiment, in accordance with the principles of the present disclosure, a surgical system is provided. The surgical system includes a first template comprising a first shaft extending along a first axis between a first proximal end and a first distal end. The first template comprises a first engagement portion configured for insertion between vertebrae of a patient. The first engagement portion comprises a first rod extending from the first distal end at an acute angle relative to the first axis and a first head coupled to the first rod. The first head comprises a first cylindrical wall having a first diameter. A second template comprises a second shaft extending along a second axis between a second proximal end and a second distal end. The second template comprises a second engagement portion configured for insertion between the vertebrae. The second engagement portion comprises a second rod extending from the second distal end at an acute angle relative to the second axis and a second head coupled to the second rod. The second head comprises a second cylindrical wall having a second diameter. The first diameter is different than the second diameter.

In one embodiment, in accordance with the principles of the present disclosure, a surgical system is provided. The surgical system includes a spinal implant template comprising a shaft extending along an axis between a proximal end and a distal end, the proximal end including a flange. An engagement portion is configured for insertion between vertebrae of a patient. The engagement portion comprises a rod extending from the distal end at an acute angle relative to the axis to facilitate ease of entry around a spinal cord of the patient. An image guide is attachable with the shaft and oriented relative to a sensor to communicate a signal representative of a position of the template. The image guide comprises a collar having a body and a pair of spaced apart tabs. The tabs are each deflectable relative to the body. The tabs each include an inner surface defining a cutout having a raised portion configured to receive the flange to connect the image guide with the template.

BRIEF DESCRIPTION OF THE DRAWINGS

The present disclosure will become more readily apparent from the specific description accompanied by the following drawings, in which:

FIG. 14B is a breakaway perspective, cross-sectional view of the third and fifth components of the surgical system;

FIG. 15A is a breakaway first side cross-sectional view of the third component and one embodiment of the fifth component of the surgical system;

FIG. 15B is a breakaway second side cross-sectional view of the third component and one embodiment of the fifth component of the surgical system;

FIG. 20 is a fourth graphical representation of a computer showing representations of the first and sixth components of the surgical system disposed with vertebrae, with the sixth component in the collapsed state;

FIG. 21 is a fifth graphical representation of a computer showing representations of the first and sixth components of the surgical system disposed with vertebrae, with the sixth component in the expanded state;

FIG. 22 is a sixth graphical representation of a computer showing representations of the first and sixth components of the surgical system disposed with vertebrae, with the sixth component in the collapsed state;

FIG. 23 is a seventh graphical representation of a computer showing representations of the first and sixth components of the surgical system disposed with vertebrae, with the sixth component in the expanded state;

FIG. 24 is an eight graphical representation of a computer showing a representation of the first component of the surgical system disposed with vertebrae;

FIG. 25 is a ninth graphical representation of a computer showing representations of the first and sixth components of the surgical system disposed with vertebrae;

FIG. 26 is a tenth graphical representation of a computer showing representations of the first and sixth components of the surgical system disposed with vertebrae;

DETAILED DESCRIPTION

Figure 1:
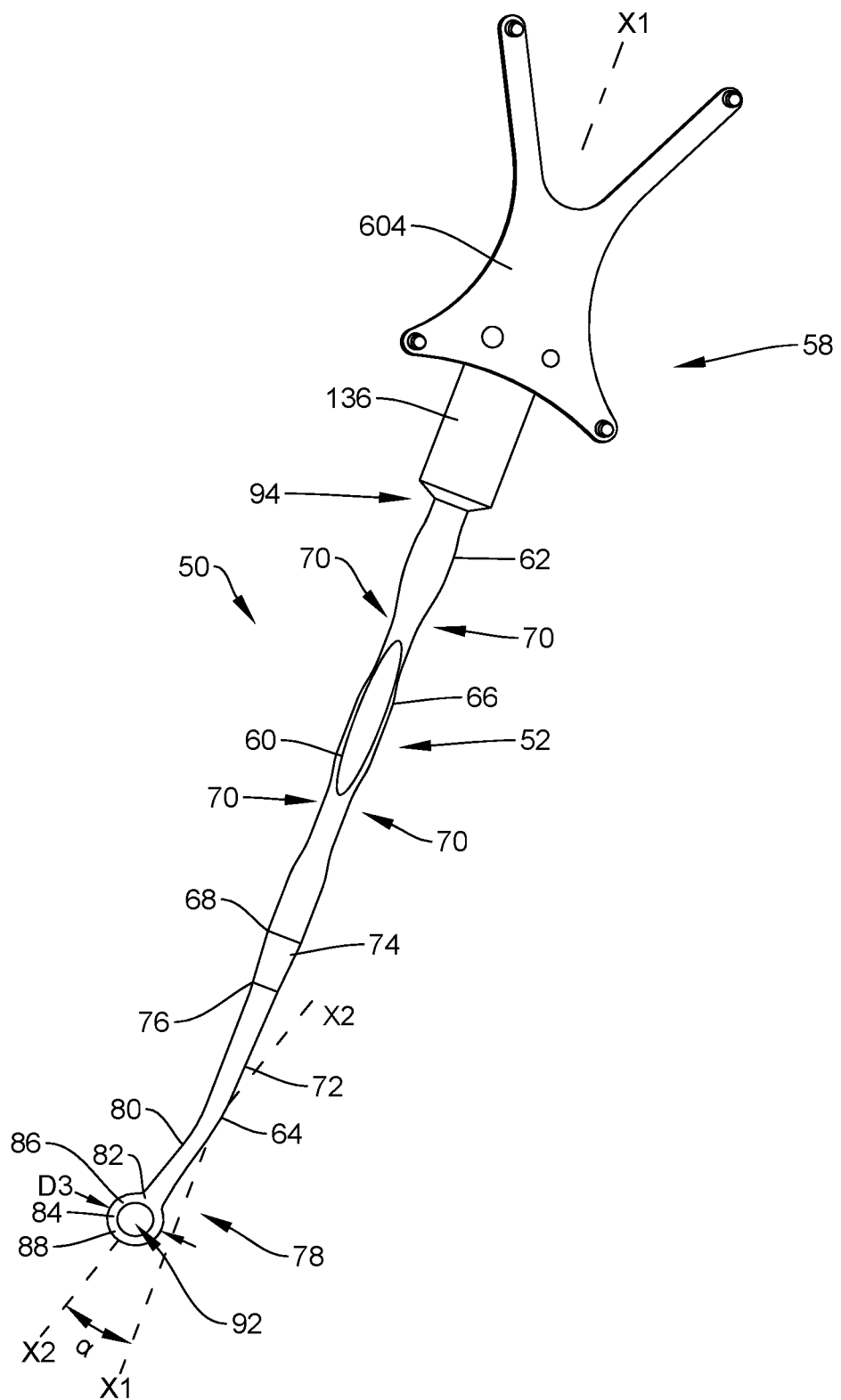
FIG. 1 is a perspective view of components of a surgical system in accordance with the principles of the present disclosure.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system includes a plurality of distinct navigated templates, such as, for example, four navigated templates. The templates include features compatible with an image guide, such as, for example, a navigation component, to connect the navigation component with the templates. In some embodiments, the templates can be used in two separate approaches, such as, for example, a posterior approach and a lateral approach. In some embodiments, the templates can be used in three separate approaches, such as, for example, an anterior approach, a lateral approach and a posterior approach.

In the posterior approach, three templates are used. The three templates have varying size cylindrical geometries that are each representative of a spinal implant, such as, for example, a corpectomy implant or cage. In some embodiments, the templates are relatively short templates. At least one of the templates includes angulation proximal to a cylindrical sizing feature to allow for insertion of the cylindrical sizing feature into a defect space, such as, for example, a corpectomy defect, while facilitating ease of entry around the spinal cord. The templates are moved against the adjacent vertebral body end plates, as well as throughout the defect space, to ensure enough bone and/or disc material is removed so that the representative cage size could fit into the defect space with the cage in a selected trajectory. The navigated templates can be used to identify key landmarks within the corpectomy defect, provide tactile feedback, and confirm the amount of resection.

In the lateral approach, either three angled templates, or an extended length template with a rectangular geometry representative of additional end cap options of the cage, are used in a lateral trajectory. The extended length template is moved against the adjacent the adjacent vertebral endcaps, and up against the lateral annulus, to ensure bone and/or disc is removed for intended final placement of the representative endcap size.

In some embodiments, the templates include features to interface with the image guide, such as for example, NAV-LOCK™ interface features sold by Medtronic Navigation, Inc. having a place of business in Louisville, Colo., that are oriented such that the image guide is parallel to the plane created by the top or bottom of the instruments, allowing for proper insertion of the templates into the defect space, with the top/bottom faces parallel to the vertebral body endcaps, and easy to view from a camera system connected with the image guide.

When navigating the angled templates, the orientation of the angle can be selected for a surgeon's need via a software menu, allowing for 180 degree rotation of the instrument being visualized.

The navigated templates have verification features of varying geometries and non-symmetric cross-sections that allow for verification with the navigated software. For example, in some embodiments, the navigated templates can include one or more verification features, such as, for example, bosses that are configured to be seated in a navigation verification divot of an implanted navigated component to allow for verification of the navigated templates with the navigation software. In some embodiments, the verification features are rectangular in a fashion that allows for seating within the navigation verification divot. In some embodiments, the verification features maintain a circular arc length from the cylindrical implant sizing geometry.

The navigation of the templates allows for visual representation of the templates within the patient's anatomy. The image guide interfaces with a computer having software features that include estimation of appropriate final implant sizing, defect height sizing, estimation of implant position and trajectory in fully collapsed and fully expanded states and/or intermediate states between the fully collapsed and fully expanded states. The software also allows for visualization of anatomy during implant sizing estimation by allowing the user the ability to save plans of the implant position and trajectory.

The software allows for estimation of appropriate final implant sizing through two methods. The first method includes manual implant size estimation using the cylindrical sizing feature of the template. The cylindrical sizing feature can be representative of an implant size, chosen by diameter and height, either in a collapsed or expanded state through use of a toggle button, for example. Toggling of the collapsed and expanded states of the implant allows the surgeon to see if the largest expanded state of the implant or cage can span the corpectomy defect space. The defect space is represented by the vertebral body height if a post-corpectomy image scan is not performed. The virtual implant and additional implants can be toggled on or off, different sizes can be selected, and the direction of the projections can be flipped 180 degrees.

In the second method, two separate projections can be saved at each of the opposite ends of the defect space. The software will then measure the resultant defect height, the angulation between coronal and sagittal planes, and the appropriate implant size for use in the defect. Angulation data from the software feature can be used to select a corresponding implant addition of a similar angle from the system offerings. The projections and navigated representations of the templates allow for ease of visualization through projections with a central cavity. The saved projections representing the cylindrical and rectangular implant can be used to plan ideal placement and trajectory during actual implant insertion. Additionally, the implant can be combined with multiple types of implant additions in varying geometries and sizes.

In some embodiments, the template virtual geometry can be used within the software to erase the resected vertebral body by moving the physical template within the resected space and removing the material from the visual representation of the patient's anatomy.

In some embodiments, the implant is inserted into the defect space using a surgical instrument, such as, for example, one or a plurality of inserters. In some embodiments, the surgical system includes three distinct navigated inserters of varying lengths, sizes and angularity. These inserters are intended for use with two separate approaches, with varying size implants. The navigated inserters have a fixed tracker geometry extended from bodies of the inserters and perpendicular to the plane of attachment of the varying implants. The perpendicularity allows for proper placement of the implant or cage while maintaining optimal visibility to a camera of the surgical system. On the navigated inserter, the geometry of the image guide is oriented at a 20 degree offset angle from the implant attachment plane.

One of the inserters is an angled inserter and one of the inserters is a longer length straight inserter. These inserters share verification features at the implant interface tip. The tip geometry, with a round on one edge of the instrument, allows for seating into the navigated verification divot. The third inserter is a shorter navigated inserter and is straight. The tip geometry of the third inserter is less wide and also allows the instrument to sit within the navigated verification slot. All three navigated inserters also have specific markings to indicate use of proper tip geometry for interface with the navigated verification divot. Additionally, the implant tip geometry and software angular verification threshold on the angled inserter, and the straight inserters, allow for verification when the inserter body is parallel to the verification divot central axis, or when the inserter body is offset from the verification divot central axis.

The posterior approach uses any of the three navigated inserters. The two straight inserters allow for direct insertion of an implant into the corpectomy defect space. The navigated angled inserter, with an angulation proximal to the implant attachment interface, allows for insertion into the defect space while facilitating ease of entry around the spinal cord. The lateral approach utilizes the longest navigated straight inserter. It allows for direct insertion of the implant into the corpectomy defect space from a lateral trajectory.

The navigation of the inserters allows for visual representation in posterior and lateral approaches in multiple anatomical views of the inserters, implants and projections relative to the patient's anatomy. The software features include estimation of appropriate final implant sizing, estimation of appropriate implant placement and trajectory, and visualization of expansion direction of the implant. It also allows easy visualization and distinction of implants and projections while estimating size, position, and trajectory with multiple implant and implant additions in multiple states of representation.

The software allows for estimation of appropriate final implant sizing through representation of the implant in a collapsed or expanded state. The intended direction of expansion of the implant can be represented by a colored portion different than the main body of the implant. Geometries of varying color and/or transparency allow for easy visualization of anatomy while navigating. Varying transparency and coloration also provide a visual way to communicate to surgeons hardware components that are only being provided for trajectory and sizing guidance, not accurately navigated.

In some embodiments, the inserter, the implant and implant additions are navigated where multiple planes in a similar anatomical view are visible at once. This allows the surgeon to visualize where the implant is within the defect space. In addition to navigating the inserter and the implants of varying sizes, projections may show implant additions of varying cylindrical and rectangular geometries and of varying degrees of geometric and/or mechanical detail. The navigation software also allows for visualization in the lateral approach of the implant and varying sizes of implant additions across the vertebral body in order to get appropriate placement and ensure the implant additions do not protrude out of the lateral annulus or lateral border of the vertebral body.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-40, there are illustrated components of a surgical system, such as, for example, a surgical system 50.

The components of surgical system 50 can be fabricated from biologically acceptable materials suitable for medical applications, including metals, synthetic polymers, ceramics and bone material and/or their composites. For example, the components of surgical system 50, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 50 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 50 may be monolithically formed, integrally connected or include fastening elements and/or instruments, as described herein.

Surgical system 50 is employed, for example, with a fully open surgical procedure, a minimally invasive procedure including percutaneous techniques, and mini-open surgical techniques to deliver and introduce instrumentation and/or a spinal implant, such as, for example, a corpectomy cage, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

System 50 includes a plurality of surgical instruments, such as, for example, a template 52 (e.g., FIG. 1), a template 54 (e.g., FIG. 12) and/or a template 56 (e.g., FIG. 11) and an image guide, such as, for example, a navigation component 58 that is removably attachable with templates 52, 54, 56, as discussed herein. Navigation component 58 is configured to allow for visualization of templates 52, 54, 56 within a patient's anatomy. Navigation component 58 interfaces with a computer having software configured to estimate the appropriate final implant sizing, defect height sizing, and estimation of implant position and trajectory in full and collapsed states, as discussed herein. In some embodiments, system 50 includes other templates in place of or in addition to templates 52, 54, 56, such as, for example, templates having different sizes and/or geometries than templates 52, 54, 56.

Figure 2:
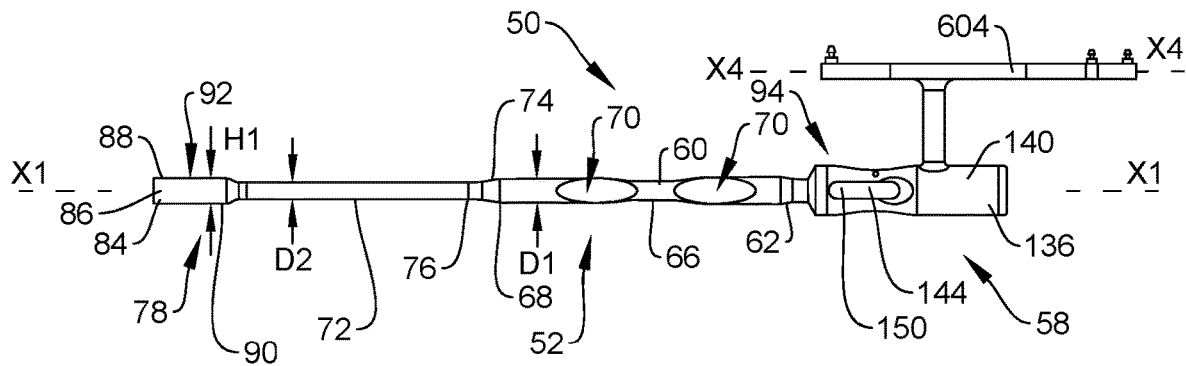
FIG. 2 is a side view of first and second components of the surgical system shown in FIG. 1.
Figure 3:
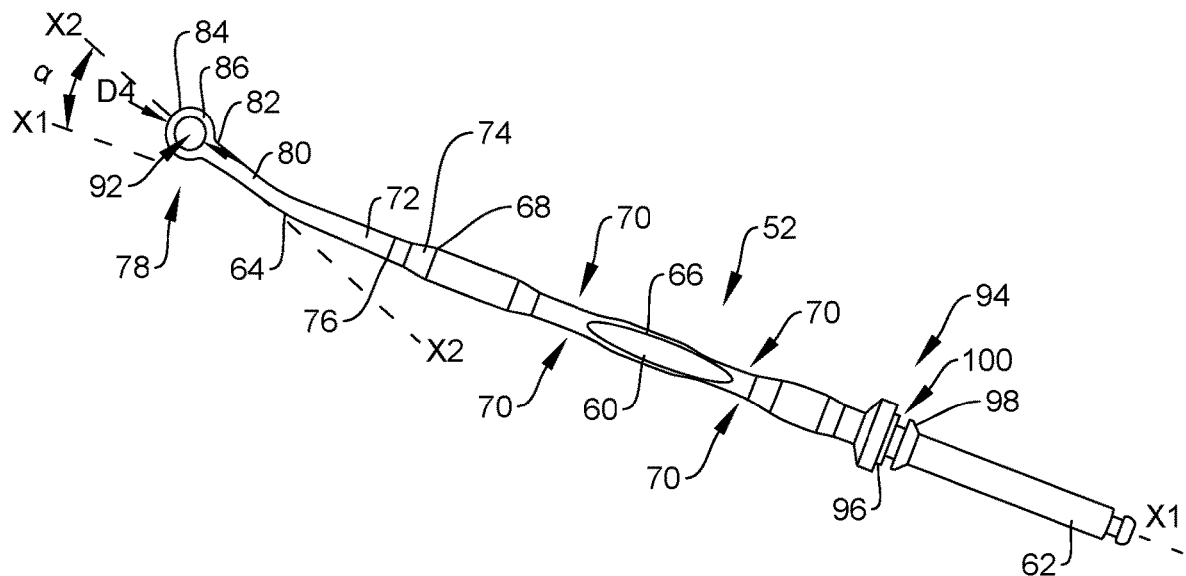
FIG. 3 is a perspective view of the first component of the surgical system shown in FIG. 1.

Template 52 includes a shaft 60 extending along a longitudinal axis X1 between a proximal end 62 and an opposite distal end 64. In various embodiments, shaft 60 is coaxial with axis X1 along the entire length of shaft 60. In some embodiments, shaft 60 includes a body 66 extending from end 62 to an end 68 between end 62 and end 64. Body 66 may include one or a plurality of recesses 70 along the length of body 66 to facilitate gripping of shaft 60. Shaft 60 includes a stem 72 that is connected to body 66 by a section 74 in various embodiments. Section 74 extends from end 68 to an end 76 and stem 72 extends from end 76 to end 64. Section 74 can be tapered from end 68 to end 76, as shown in FIG. 1. In some embodiments, section is continuously tapered from end 68 to end 76 such that stem 72 has a diameter that is less than a diameter of body 66 to facilitate insertion of stem 72 into a surgical site, such as, for example, a corpectomy defect. For example, in some embodiments, body 66 has a maximum diameter D1 that is greater than a maximum diameter D2 of stem 72, as shown in FIG. 2. This allows body 66 to be large enough to facilitate gripping by a medical practitioner, while a permitting stem 72 to be small enough to be inserted into a corpectomy defect. In some embodiments, stem 72 has a uniform diameter along the entire length of stem 72. In some embodiments, stem 72 is tapered and has a diameter adjacent to end 64 that is less than a diameter adjacent to end 76. In some embodiments, stem 72 is continuously tapered from end 76 to end 64. In some embodiments, shaft 60 has a solid configuration that is free of any cavities or openings to provide strength and/or rigidity to shaft 60.

Template 52 includes an engagement portion 78 adjacent to end 64. Portion 78 is configured for insertion between adjacent vertebrae of a patient, or insertion within a corpectomy defect. Portion 78 includes a rod 80 that extends from end 64 to an end 82 along a longitudinal axis X2. Axis X2 extends at an angle α relative to axis X1 to facilitate insertion of portion 78 around a spinal cord of a patient, as discussed herein. In some embodiments, angle α is greater than 0°. In some embodiments, angle α is an acute angle. In some embodiments, angle α is an oblique angle. In some embodiments, angle α is between about 1° and about 90°. In some embodiments, angle α is between about 1° and about 45°. In some embodiments, angle α is between about 20° and about 40°.

Figure 4:
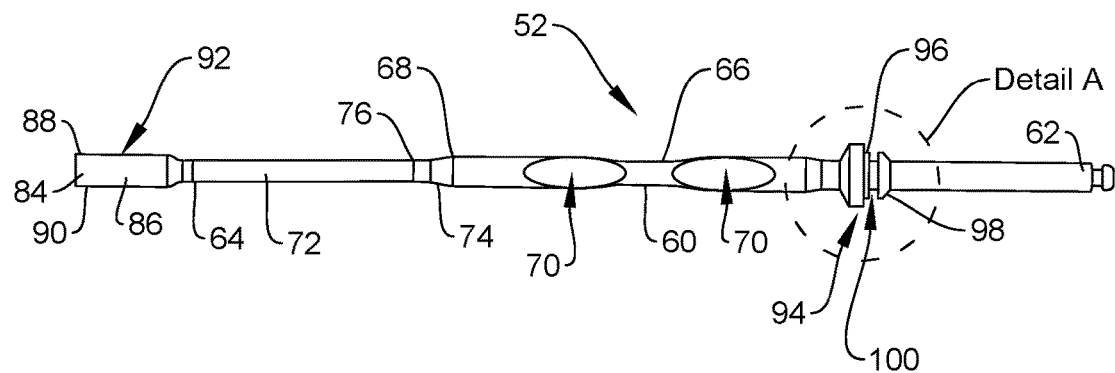
FIG. 4 is a side view of the first component of the surgical system shown in FIG. 1.

Portion 78 includes a head 84 that extends from end 82. Head 84 is configured to be positioned in the corpectomy defect to represent sizing of an implant to be inserted into the corpectomy defect, as discussed herein. Head 84 includes a wall 86 having a top surface 88 and an opposite bottom surface 90, as best shown in FIGS. 2 and 4. The distance between surface 88 and surface 90 defines a height H1 of head 84. In some embodiments, wall 86 has a cylindrical configuration and defines an opening 92 that extends through the thickness of head 84. That is opening 92 extends continuously between and through surface 88 and surface 90. In some embodiments, height H1 is greater than diameter D2. In some embodiments, height H1 is greater than or equal to diameter D1. In some embodiments, height H1 is less than diameter D1. The size and shape of wall 86 and/or opening 92 are configured to correspond to the size and shape of an implant to be inserted into the corpectomy defect to determine if the implant is suitable for implantation into the corpectomy defect, or if an implant of a different size and shape would be more suitable for implantation into the corpectomy defect, as discussed herein. In some embodiments, wall 86 has a maximum outer diameter D3, as shown in FIG. 1, and a maximum inner diameter D4, as shown in FIG. 4. In some embodiments, wall 86 and/or opening 92 can be variously shaped, such as, for example, circular, oval, oblong, triangular, square, polygonal, irregular, uniform, non-uniform, offset, staggered, undulating, arcuate, variable and/or tapered.

In some embodiments, head 84 is monolithically and/or integrally formed with shaft 60 to provide increased strength and/or rigidity to template 52. In some embodiments, head 84 is removably coupled to shaft 60 to allow different heads, such as, for example, heads having different sizes or shapes to be coupled to shaft 60. It is envisioned that allowing different heads to be coupled to shaft 60 will reduce the number of instruments needed to perform a given procedure. Indeed, rather than having a plurality of shafts, with each of the shafts having a different head coupled thereto, there could be only one shaft and a plurality of heads that can be removably coupled to the shaft.

Figure 5:
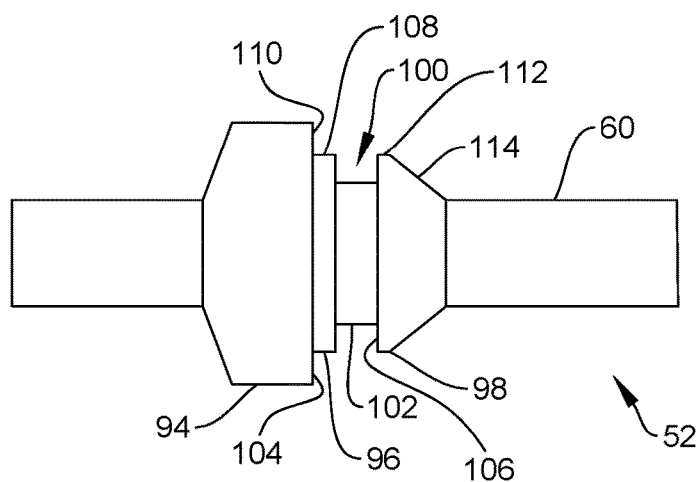
FIG. 5 is an enlarged view of detail A shown in FIG. 4.

Shaft 60 includes a hub 94 positioned between end 62 and end 68. Hub 94 includes a flange 96 and a flange 98 that is spaced apart from flange 96. Hub 94 includes a recess 100 between flanges 96, 98. Recess 100 is defined by an outer surface 102 of shaft 60, a surface 104 of flange 96 and a surface 106 of flange 98, as best shown in FIG. 5. In various embodiments, surface 102 extends parallel to axis X1 and surfaces 104, 106 extend perpendicular to axis X1. Flange 96 includes a surface 108 positioned between surface 104 and a surface 110 of hub 94. Surface 108 extends parallel to axis X1 and surface 110 extends perpendicular to axis X1. Flange 98 includes a surface 112 positioned between surface 106 and a surface 114 of flange 98. Surface 112 extends parallel to axis X1 and surface 114 extends perpendicular to axis X1. In some embodiments, surface 104 is configured to act as a ramp to connect navigation component 58 with shaft 60, as discussed herein. In some embodiments, surface 104, surface 106, surface 108, surface 110, surface 112 and/or surface 114 may be disposed at alternate orientations, relative to axis X1, such as, for example, parallel, transverse, perpendicular and/or other angular orientations such as acute or obtuse, co-axial and/or may be offset or staggered.

Figure 6:
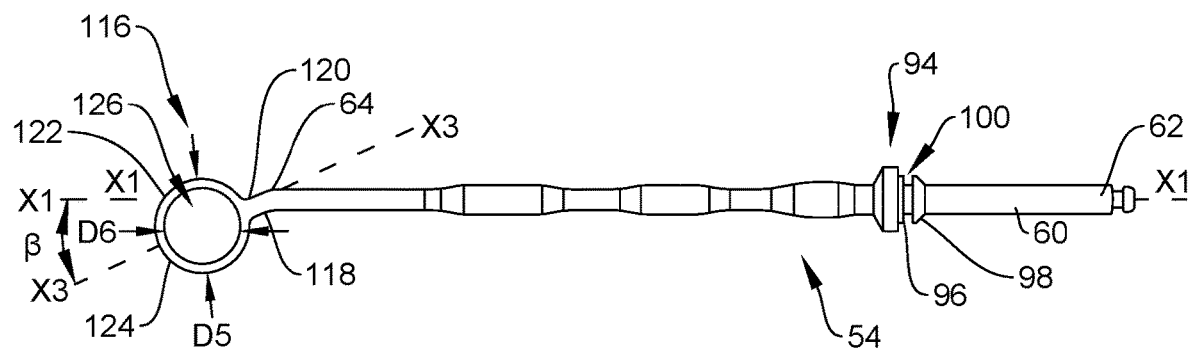
FIG. 6 is a perspective view of a third component of the surgical system shown in FIG. 1.

Template 54 is similar to template 52 and includes shaft 60 with hub 94 positioned between end 62 and end 64, as shown in FIG. 6. Template 54 includes an engagement portion 116 having a rod 118 that is similar to rod 80 extending from end 64. Rod 118 extends from end 64 to an end 120 along a longitudinal axis X3. Axis X3 extends at an angle β relative to axis X1 to facilitate insertion of portion 116 around a spinal cord of a patient, as discussed herein. In some embodiments, angle β is greater than 0°. In some embodiments, angle β is an acute angle. In some embodiments, angle β is an oblique angle. In some embodiments, angle β is between about 1° and about 90°. In some embodiments, angle β is between about 1° and about 45°. In some embodiments, angle β is between about 20° and about 40°. In some embodiments, angle β is less than or equal to angle α. In some embodiments, angle β is greater than or equal to angle α. In some embodiments, angle β is different than angle α. In some embodiments, the maximum length of rod 118 is less than the maximum length of rod 80. It is envisioned that the differences between the lengths of rod 80 and rod 118 and the difference between angle α and angle β provides a medical practitioner with options regarding which instrument to use for a given procedure. For example, the medical practitioner can choose either template 52 or template 54 depending on which has the greater angulation, where increased angulation is required to facilitate insertion around the spinal cord of a patient.

Portion 116 includes a head 122 that extends from end 120. Head 122 is similar to head 84 and is configured to be positioned in the corpectomy defect to represent sizing of an implant to be inserted into the corpectomy defect, as discussed herein. Head 122 includes a wall 124 having a cylindrical configuration and defines an opening 126 that extends through the thickness of head 122. That is, opening 126 extends continuously between and through opposite top and bottom surfaces of head 122. The size and shape of wall 124 and/or opening 126 are configured to correspond to the size and shape of an implant to be inserted into the corpectomy defect to determine if the implant is suitable for implantation into the corpectomy defect, or if an implant of a different size and shape would be more suitable for implantation into the corpectomy defect, as discussed herein. In some embodiments, wall 124 has a maximum outer diameter D5 and a maximum inner diameter D6. In some embodiments, diameter D3 is less than diameter D5 and diameter D4 is less than diameter D6. Template 54 may therefore be used to approximate the positioning of larger implants, while template 52 may be used to approximate the positioning of smaller implants. However, it is envisioned that the length of rod 80 or rod 118, the inner diameter of head 84 or head 122 and/or the outer diameter of head 84 or head 122 can be selected based on the size and configuration of the implant to be positioned in the corpectomy defect. In some embodiments, wall 124 and/or opening 126 can be variously shaped, such as, for example, oval, oblong, triangular, square, polygonal, irregular, uniform. In some embodiments, head 122 is monolithically and/or integrally formed with shaft 60 to provide increased strength and/or rigidity to template 54. In some embodiments, head 122 is removably coupled to shaft 60 to allow different heads, such as, for example, head 84 or head 122 to be coupled to shaft 60 depending upon the preference of a medical practitioner.

Figure 11:
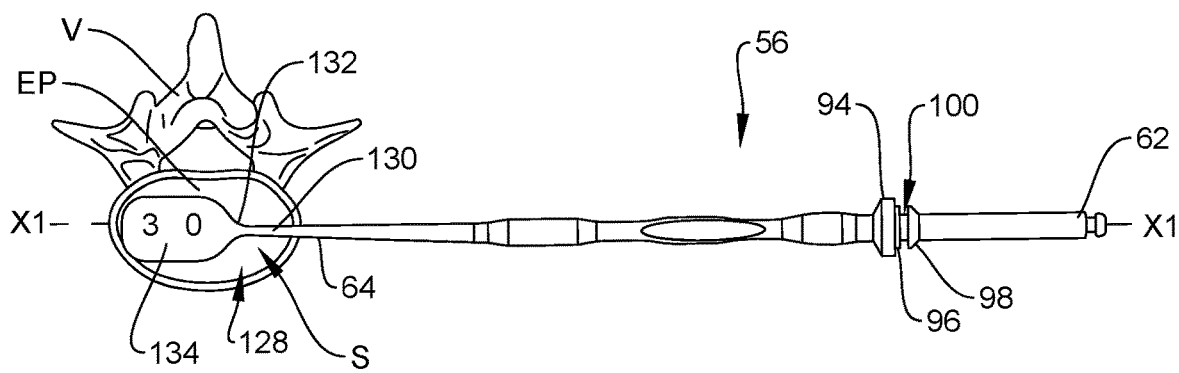
FIG. 11 is a plan view of a fourth component of the surgical system disposed with vertebrae.

Template 56 is similar to template 52 and template 54 and includes shaft 60 with hub 94 positioned between end 62 and end 64, as shown in FIG. 11. Template 56 includes an engagement portion 128 having a rod 130 that is similar to rods 80, 118 extending from end 64. Rod 130 extends from end 64 to an end 132 along axis X1. In some embodiments, the maximum length of rod 130 is less than or equal the maximum length of rod 80 and/or rod 118. In some embodiments, the maximum length of rod 130 is greater than or equal the maximum length of rod 80 and/or rod 118. Portion 128 includes a head 134 that extends from end 132. Head 134 is configured to be positioned in the corpectomy defect to represent sizing of an implant to be inserted into the corpectomy defect, as discussed herein. Head 134 has a solid wall configuration with the shape of a rounded rectangle. That is, head 134 is free of any recesses, holes or apertures. In some embodiments, head 134 can be variously shaped, such as, for example, circular, oval, oblong, triangular, square, rectangular, polygonal, irregular, uniform. It is envisioned that the size and shape of head 134 can be adapted to match or approximate the size and shape of an implant to be implanted in the corpectomy defect. In some embodiments, head 134 is monolithically and/or integrally formed with shaft 60 to provide increased strength and/or rigidity to template 56. In some embodiments, head 134 is removably coupled to shaft 60 to allow different heads, such as, for example, head 84, head 122 or head 134 to be coupled to shaft 60 depending upon the preference of a medical practitioner.

Figure 7:
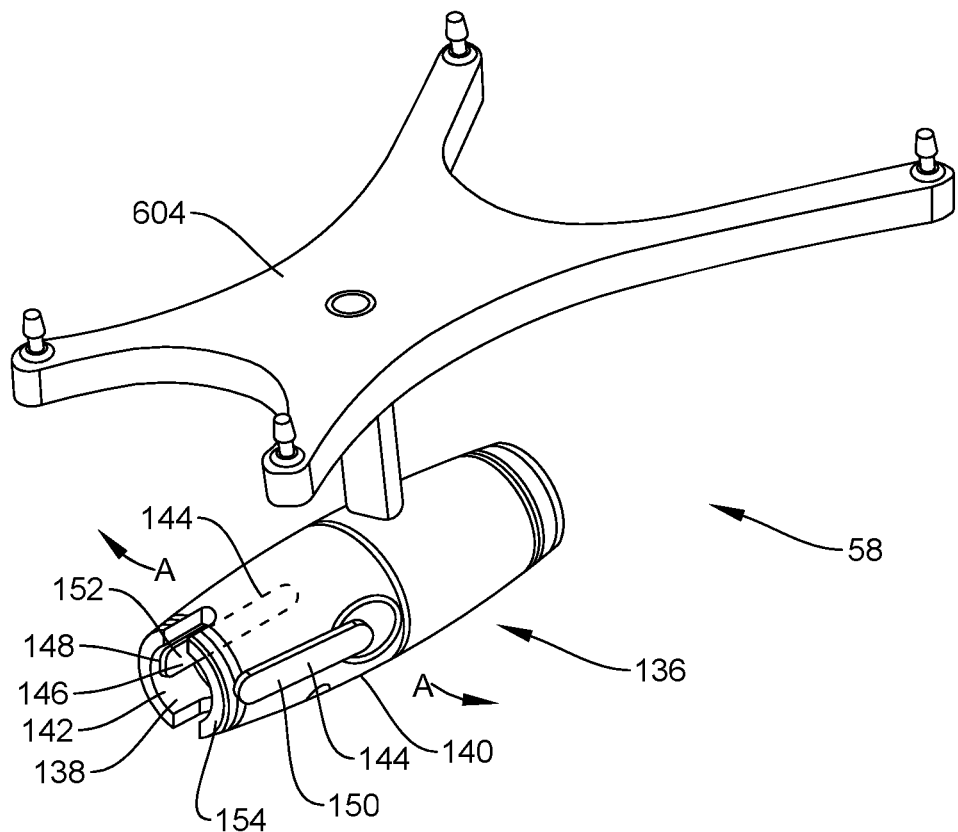
FIG. 7 is a perspective view of the second component of the surgical system shown in FIG. 1.

Navigation component 58 is configured to be coupled to hub 94 to connect navigation component 58 with template 52, template 54, or template 56. Navigation component 58 includes a collar 136 having an inner surface 138 and an outer surface 140, as best shown in FIG. 7. Surface 138 defines a passageway 142. Surface 138 is configured for releasable engagement with hub 94. Passageway 142 is configured to receive shaft 60 and a portion of hub 94. Surface 138 defines a lock, such as, for example, at least one resilient prong or tab 144. In one embodiment, collar 136 includes a plurality of tabs 144, as shown in FIG. 7. Each tab 144 includes an inner surface 146 that defines a cutout 148 and an outer surface 150. Each cutout 148 includes raised portions 152 that define edges of cutout 148. Cutout 148 is configured to receive flange 98. In its initial position, surface 150 is aligned with surface 140 of collar 136.

To connect navigation component 58 with template 52, template 54 or template 56, collar 136 is translated over shaft 60 such that flange 98 engages portions 152 and applies a force to tabs 144 to move tabs 144 outwardly, in the direction shown by arrows A in FIG. 7, such that surface 150 is deflected from surface 140. As flange 98 translates over portions 152, flange 98 moves into cutouts 148 allowing tabs 144 to move back to their initial position. In some embodiments, navigation component 58 is configured for removable engagement with template 52, template 54 and template 56. In some embodiments, navigation component 58 may be integrally formed with template 52, template 54, or template 56. In one embodiment, flange 96 is configured to engage collar 136 to reduce vibrations resulting from the torque of an actuator. In some embodiments, an end surface 154 of collar 136 directly engages surface 110 of hub 94 when flange 98 is positioned in cutouts 148 to prevent and/or reduce the amount of movement between navigation component 58 and shaft 60.

Figure 8:
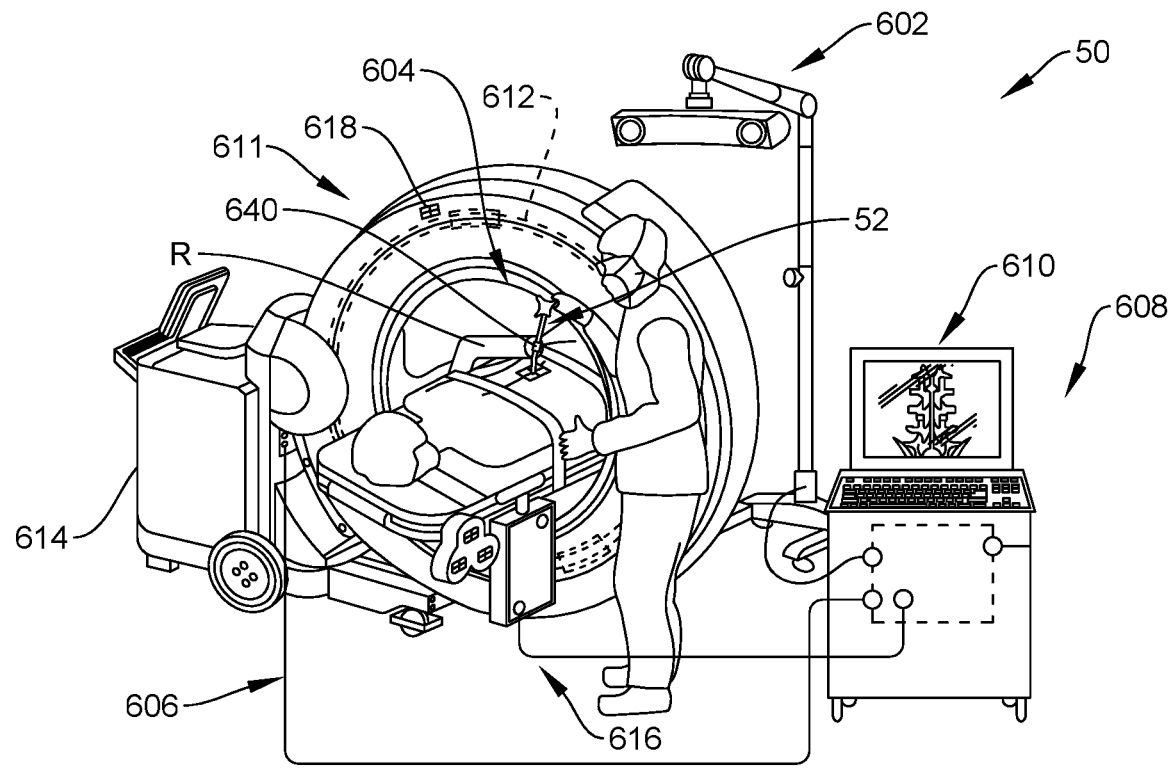
FIG. 8 is a perspective view of several components of one embodiment of the surgical system, being used by a surgeon with a patient, in accordance with the principles of the present disclosure.

Navigation component 58 includes an emitter array 604, as shown in FIG. 7. Emitter array 604 is configured for generating a signal to sensor array 602 of a surgical navigation system 606, as shown in FIG. 8. In some embodiments, the signal generated by emitter array 604 represents a position of an instrument, such as, for example, template 52, template 54, or template 56 relative to tissue, such as, for example, bone. In some embodiments, the signal generated by emitter array 604 represents a three-dimensional position of template 52, template 54, or template 56 relative to tissue. In some embodiments, emitter array 604 includes a reflectance array and/or is configured to reflect a signal to sensor array 602.

In some embodiments, sensor array 602 receives signals from emitter array 604 to provide a three-dimensional spatial position and/or a trajectory of a template 52, template 54 or template 56 relative to tissue. Emitter array 604 communicates with a processor of a computer 608 of navigation system 606 to generate data for display of an image on a monitor 610. In some embodiments, sensor array 602 receives signals from emitter array 604 to provide a visual representation of a position of template 52, template 54 or template 56 relative to and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 606 is configured for acquiring and displaying medical imaging, such as, for example, x-ray images appropriate for a given surgical procedure. In some embodiments, pre-acquired images of a patient are collected. In some embodiments, surgical navigation system 606 can include an O-ARM® imaging device 611 sold by Medtronic Navigation, Inc. having a place of business in Louisville, Colo., USA. Imaging device 611 may have a generally annular gantry housing that encloses an image capturing portion 612.

In some embodiments, navigation system 606 comprises an image capturing portion 614 that may include an x-ray source or emission portion and an x-ray receiving or image receiving portion located generally or as practically possible 180 degrees from each other and mounted on a rotor (not shown) relative to a track of image capturing portion 614. Image capturing portion 614 can be operable to rotate 360 degrees during image acquisition. Image capturing portion 614 may rotate around a central point or axis, allowing image data of the patient to be acquired from multiple directions or in multiple planes. Surgical navigation system 606 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 606 can include C-arm fluoroscopic imaging systems, which can generate three-dimensional views of a patient. The position of image capturing portion 614 can be precisely known relative to any other portion of an imaging device of navigation system 606. In some embodiments, a precise knowledge of the position of image capturing portion 614 can be used in conjunction with a tracking system 616 to determine the position of image capturing portion 614 and the image data relative to the patient.

Tracking system 616 can include various portions that are associated or included with surgical navigation system 606. In some embodiments, tracking system 616 can also include a plurality of types of tracking systems, such as, for example, an optical tracking system that includes an optical localizer, such as, for example, sensor array 602 and/or an EM tracking system that can include an EM localizer. Various tracking devices can be tracked with tracking system 616 and the information can be used by surgical navigation system 606 to allow for a display of a position of an item, such as, for example, a patient tracking device, an imaging device tracking device 618, and an instrument tracking device, such as, for example, emitter array 604, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to a computer 614 where they may be forwarded to computer 608. Image transfer may be performed over a standard video connection or a digital link including wired and wireless. Computer 608 provides the ability to display, via monitor 610, as well as save, digitally manipulate, or print a hard copy of the received images. In some embodiments, images may also be displayed to the surgeon through a heads-up display.

In some embodiments, surgical navigation system 606 provides for real-time tracking of the position of template 52, template 54, or template 56 relative to tissue. Sensor array 602 is located in such a manner to provide a clear line of sight with emitter array 604, as described herein. In some embodiments, fiducial markers of emitter array 604 communicate with sensor array 602 via infrared technology. Sensor array 602 is coupled to computer 608, which may be programmed with software modules that analyze signals transmitted by sensor array 602 to determine the position of each object in a detector space.

In some embodiments, template 52, template 54, or template 56 are configured for use with a guide member, such as, for example, an end effector 640 of a robotic arm R. End effector 640 defines a channel configured for disposal of template 52, template 54, or template 56. Robotic arm R includes position sensors (not shown), similar to those referenced herein, which measure, sample, capture and/or identify positional data points of end effector 640 in three-dimensional space for a guide-wireless insertion of template 52, template 54, or template 56. In some embodiments, the position sensors of robotic arm R are employed in connection with surgical navigation system 606 to measure, sample, capture and/or identify positional data points of end effector 640 in connection with surgical treatment, as described herein. The position sensors are mounted with robotic arm R and calibrated to measure positional data points of end effector 640 in three dimensional space, which are communicated to computer 608.

Figure 9:
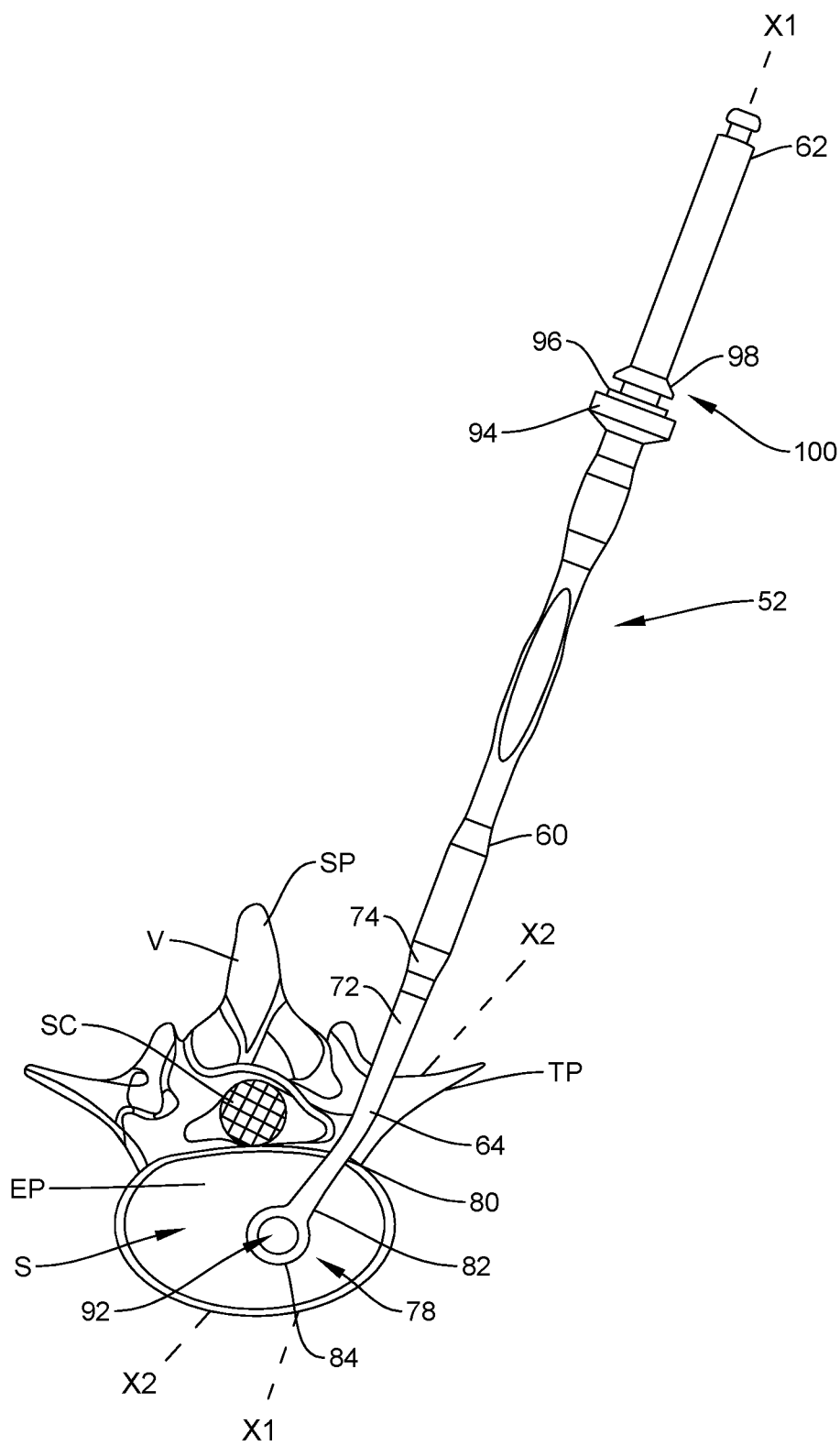
FIG. 9 is a first plan view of the first component of the surgical system shown in FIG. 1 disposed with vertebrae.
Figures 16, 17:
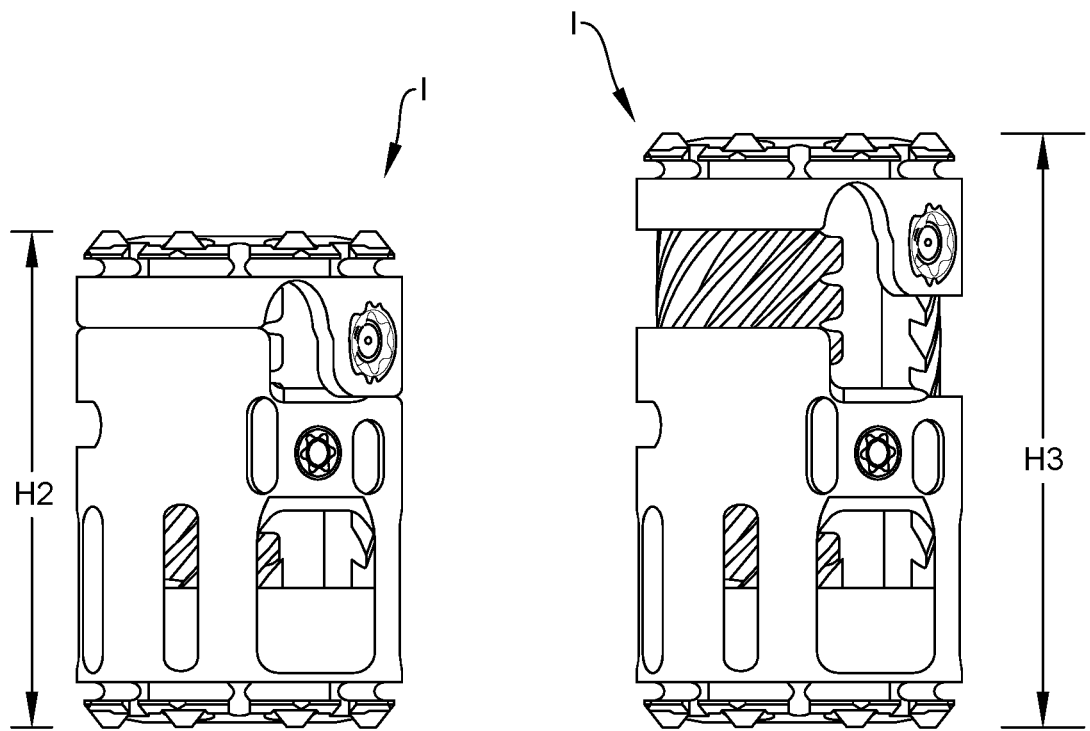
FIG. 16 is a first side view of a sixth component of the surgical system, with the fifth component in a collapsed state.
FIG. 17 is a second side view of the sixth component of the surgical system, with the sixth component in an expanded state.

In assembly, operation and use, navigation component 58 is connected with template 52, as discussed herein, and template 52 is inserted into a corpectomy defect space S of a vertebra V using a posterior approach such that engagement portion 78 moves around a spinal cord SC for positioning in space S and stem 72 is positioned between a spinous process SP of vertebra V and a transverse process TP of vertebra V, as shown in FIG. 9. Navigation component 58 has been omitted from FIG. 9, for clarity. Shaft 60 is manipulated to move head 84 such that surface 90 moves against an end plate EP of vertebra V. In some embodiments, shaft 60 is manipulated to move head 84 such that surface 88 moves against an end plate of a vertebra that is superior to vertebra V and defines a portion of space S. Head 84 is moved against the end plates and/or the lateral annuluses of the vertebrae as well as throughout space S to remove bone and/or disc material within space S. In some embodiments, head 84 is moved throughout space S to remove enough bone and/or disc material within space S to fit an implant, such as, for example, implant I within space S in an intended position and an intended trajectory. For example, in some embodiments, implant I is movable between a collapsed state, as shown in FIG. 16, and an expanded state, as shown in FIG. 17. Implant has a height H2 when implant I is in the collapsed state and an increased height H3 when implant I is in the expanded state. As such, head 84 is moved throughout space S to remove enough bone and/or disc material within space S to fit implant I in space S when implant I is in the collapsed state, the expanded state, or a state in between the collapsed state and the expanded state wherein implant I has a height between height H2 and height H3. In some embodiments, head 84 includes a blade or other sharpened surface to facilitate cutting and/or scraping of tissue, such as, for example, bone and/or disc material. In some embodiments, template 52 is used to identify key landmarks within space S, provide tactile feedback, and confirm the amount of resection via navigation component 58 and surgical navigation system 606, as discussed herein. In some embodiments, implant I is the same or similar to one or more of the implants disclosed in U.S. patent application Ser. No. 14/510,895, filed Oct. 9, 2014, which is expressly incorporated herein by reference, in its entirety.

Figure 10:
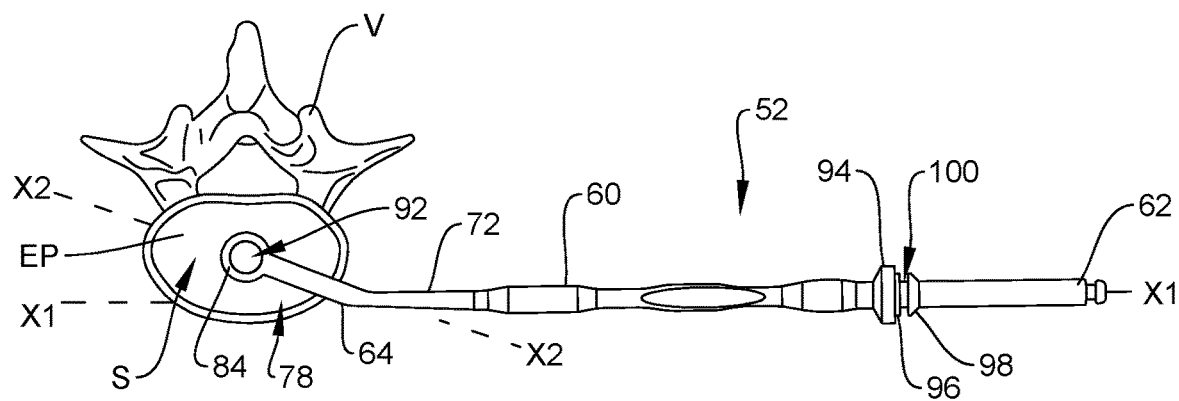
FIG. 10 is a second plan view of the first component of the surgical system shown in FIG. 1 disposed with vertebrae.

In some embodiments, navigation component 58 is connected with template 52, as discussed herein, and template 52 is inserted into space S of vertebra V using a lateral approach such that engagement portion 78 is positioned in space S, as shown in FIG. 10. Navigation component 58 has been omitted from FIG. 10, for clarity. Shaft 60 is manipulated to move head 84 such that surface 90 moves against an end plate EP of vertebra V. In some embodiments, shaft 60 is manipulated to move head 84 such that surface 88 moves against an end plate of the vertebra that is superior to vertebra V and defines a portion of space S. Head 84 is moved against the end plates and/or the lateral annuluses of the vertebrae as well as throughout space S to remove bone and/or disc material within space S. In some embodiments, head 84 is moved throughout space S to remove enough bone and/or disc material within space S to fit an implant, such as, for example, implant I within space S in an intended position and an intended trajectory.

In some embodiments, navigation component 58 is connected with template 56, as discussed herein, and template 56 is inserted into space S of vertebra V using a lateral approach such that engagement portion 128 is positioned in space S, as shown in FIG. 11. Navigation component 58 has been omitted from FIG. 11, for clarity. Shaft 60 is manipulated to move head 134 such that head 134 moves against end plate EP of vertebra V. In some embodiments, shaft 60 is manipulated to move head 134 moves against the end plates and the lateral annuluses of the vertebrae as well as throughout space S to remove bone and/or disc material within space S. In some embodiments, head 134 is moved throughout space S to remove enough bone and/or disc material within space S to fit an implant, such as, for example, implant I within space S in an intended position and an intended trajectory. Head 134 has rectangular geometry that is representative of end plate options of implant I. For example, one or more end plates can be used in connection with implant I. The end plates of implant I can have different geometries, such as, for example, rectangular, oval, circular, square, etc. Head 134 can thus be adapted to have a geometry that matches the geometry of the end plates of implant I to approximate the position of the end plates within space S.

Figure 12:
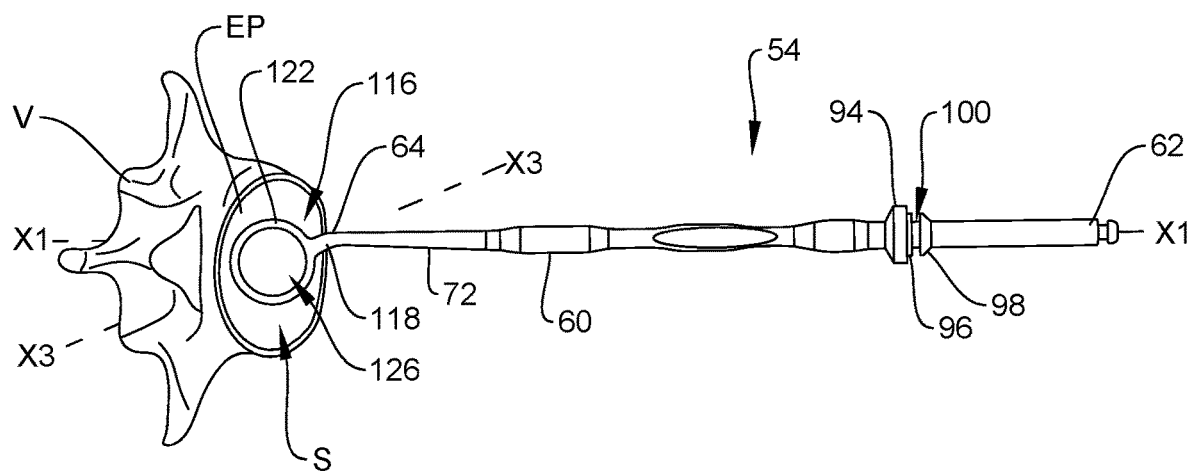
FIG. 12 is a plan view of the third component of the surgical system disposed with vertebrae.

In some embodiments, navigation component 58 is connected with template 54, as discussed herein, and template 54 is inserted into space S of vertebra V using a lateral approach such that engagement portion 116 is positioned in space S, as shown in FIG. 12. Navigation component 58 has been omitted from FIG. 12, for clarity. Shaft 60 is manipulated to move head 122 such that head 122 moves against end plate EP of vertebra V. In some embodiments, shaft 60 is manipulated to move head 122 such that head 122 moves against an end plate of the vertebra that is superior to vertebra V and defines a portion of space S. Head 122 is moved against the end plates and the lateral annuluses of the vertebrae as well as throughout space S to remove bone and/or disc material within space S. In some embodiments, head 122 is moved throughout space S to remove enough bone and/or disc material within space S to fit an implant, such as, for example, implant I within space S in an intended position and an intended trajectory.

Navigation component 58 is connected with template 52, template 54 and/or template 56 such that an axis X4 defined by emitter array 604 such that axis X4 is parallel with axis X1, as shown in FIG. 2, for example. This allows for proper insertion of template 52, template 54 and/or template 56 into space S, with the top and bottom surfaces of heads 84, 122, 134 parallel to the end caps of the vertebrae. It is envisioned that having axis X4 parallel to axis X1 facilitates viewing from a camera system of surgical navigation system 606.

Figure 13:
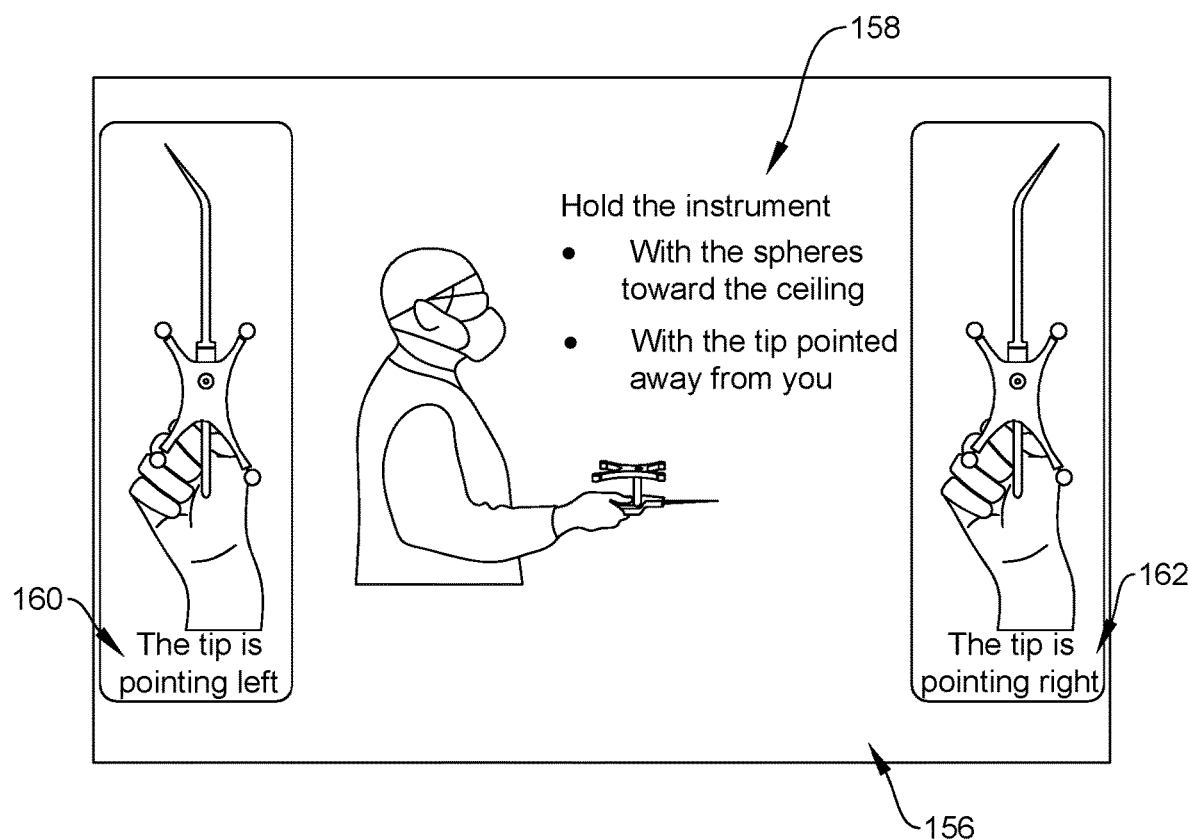
FIG. 13 is first graphical representation of a computer showing representations of the first and second components of the surgical system shown in FIG. 1.
Figure 14A:
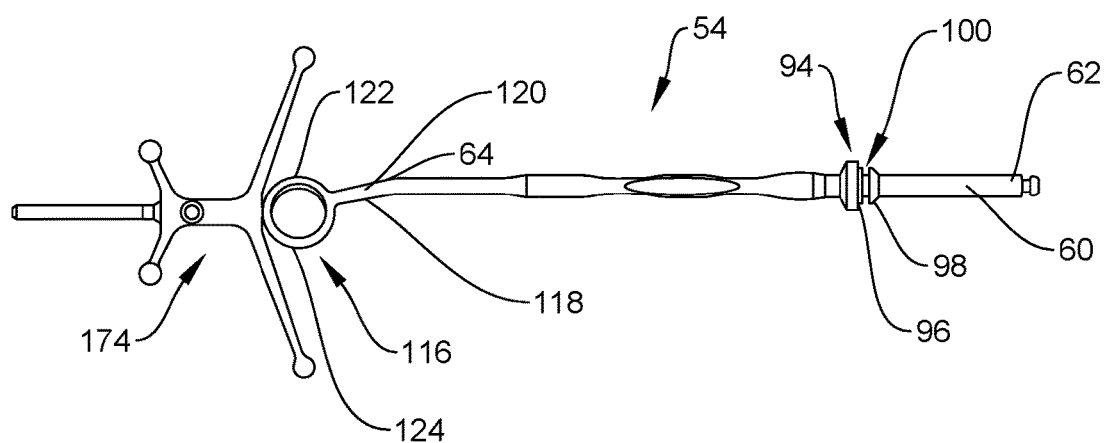
FIG. 14A is a perspective view of the third component and a fifth component of the surgical system.

In some embodiments, the orientation of angles α of template 52 and/or the orientation of angle β of template 54 can be selected using a software menu of surgical navigation system 606, such as, for example, a software menu 156 of computer 608, as shown in FIG. 13. In some embodiments, menu 156 is displayed on monitor 610. In some embodiments, menu 156 provides instructions 158 to a medical practitioner concerning how he or she should hold template 52 and/or template 54. The medical practitioner can then select either a first window 160, which orients rod 80 and/or rod 118 in a first orientation, or a second window 162, which orients rod 80 and/or rod 118 in a second orientation. This allows for 180 degree rotation of template 52 and/or template 54.

In some embodiments, template 52, template 54 and/or template 56 can include one or more verification features, such as, for example, one or more bosses 190 configured to be seated in a verification divot 192 of an implanted navigation component 194 to allow for verification with the navigation software, as shown in FIGS. 14A-15B. Boss 190 of template 54 extends outwardly from wall 124 of head 122, as shown in FIGS. 14B-15B. It is envisioned that bosses 190 of templates 52, 56 can be similarly positioned on head 84 of template 52 and head 134 of template 56. For example, boss 190 of template 52 can extend outwardly from wall 86 and boss 190 of template 52 can extend outwardly from an outer surface of head 134 of template 56. Component 194 is implanted in or adjacent to an intervertebral disc space prior to inserting head 84 of template 52, head 122 of template 54 or head 134 of template 56 into the intervertebral disc space. After component 194 is implanted in or adjacent to an intervertebral disc space, head 84 of template 52, head 122 of template 54, or head 134 of template 56 is guided into the intervertebral disc space such that boss 190 is seated within divot 192 to allow for verification with the navigation software. Boss 190 can have varying geometries and/or non-concentric cross-sections. In one embodiment, boss 190 is rectangular to allow for seating within divot 192 in a manner that prevents movement of boss 190 within divot 192, as shown in FIG. 15A. In one embodiment, boss 190 is arcuate to allow for seating within divot 192 in a manner that allows boss 190 to move within divot 192, as shown in FIG. 15A.

In some embodiments, navigation component 58 communicates with surgical navigation system 606 to provide visual representations of template 52, template 54 and/or template 56 within a patient's anatomy. In some embodiments, computer 608 includes software that provides an estimation of appropriate full implant sizing, defect height sizing, and estimation of implant position and trajectory in both fully collapsed or fully expanded states. In some embodiments, the software can be configured to determine the size of an area, such as, for example, space S, and the size of an implant, such as, for example, implant I. For example, the software can determine height H2 and/or height H3. In some embodiments, the software can create an image of space S and a representation of implant I within space S so a medical practitioner can visualize whether there is sufficient room within space S for implant I. In some embodiments, the image created by the software can show the trajectory of implant I within space S. In some embodiments, the software can adjust the trajectory of implant I within space S and provide an image representing the same so that the medical practitioner can determine the optimal trajectory of implant I within space S. In some embodiments, the software can allow visualization of anatomy during implant sizing estimation by allowing the user the ability to save plans of the implant position and trajectory.

Figures 18, 19:
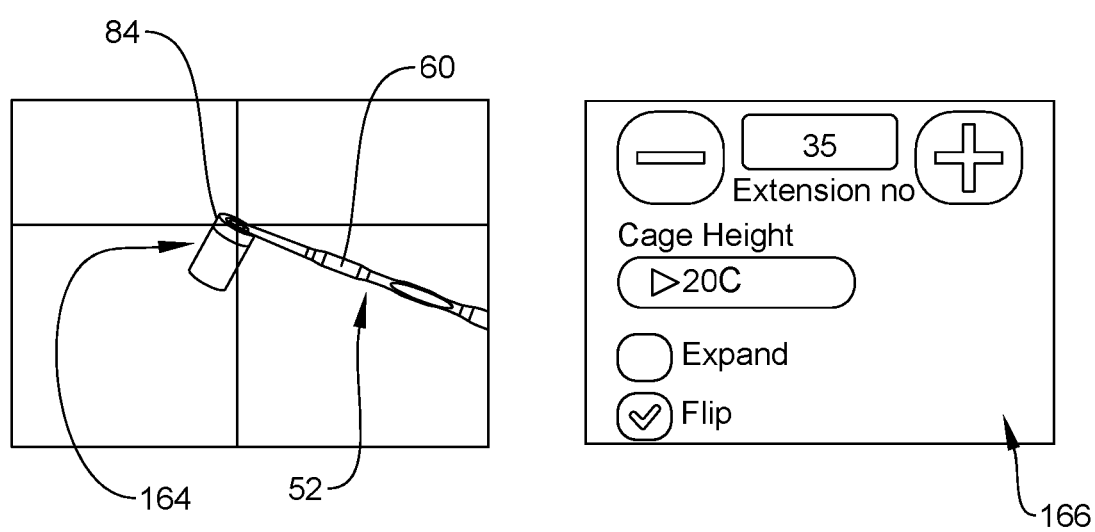
FIG. 18 is a second graphical representation of a computer showing representations of the first and sixth components of the surgical system disposed with vertebrae.
FIG. 19 is a third graphical representation of a computer showing a user interface of the surgical system.

In some embodiments, computer 608 includes software that estimates final implant system using head 84 and/or head 122. For example, head 84 and/or head 122 can be used to generate a cylindrical representation 164 that is representative of the size of implant I, as shown in FIG. 18. In some embodiments, the software is configured to generate a toggle button 166 that is viewable on monitor 610. Toggle button 166 switches representation 164 between a view having implant I in the collapsed and a view having implant I in the expanded state. This allows a medical practitioner to quickly visualize implant I within space S with implant I in both the collapsed state (FIG. 20) and the expanded state (FIG. 21) via representation 164. That is, toggling of representation 164 allows the medical practitioner to see if the largest expanded state of implant I can span the space between adjacent vertebrae.

In some embodiments, the software is configured to flip the orientation of representation 164 180 degrees. In some embodiments, the software is configured to turn representation 164 on and off. That is, the software can be configured to provide an image of template 52 within space without representation 164. If the medical practitioner then wishes to visualize how an implant, such as, for example, implant I would fit within space S, he or she can use toggle button 166 to provide an image of template 52 within space via representation 164.

In some embodiments, computer 608 includes software that estimates final implant system using a projection 168 and a projection 170 that can be saved at each of the opposite ends of space S, as shown in FIGS. 22 and 23. Projections 168, 170 represent the cylindrical geometry of an implant, such as, for example, implant I. In some embodiments, projection 168 represents the cylindrical geometry of implant I with implant I in the collapsed state and projection 170 represents the cylindrical geometry of implant I with implant I in the expanded state. The software will then measure the resultant defect height, angulation between coronal and sagittal planes, and appropriate implant size for use in space S. Angulation data from the software can be used to select a corresponding implant addition, such as, for example, one or more end plates of an implant, such as, for example, implant I. The visual representation of template 52 allows for ease of visualizations through opening 92, as shown in FIG. 24.

Figure 27:
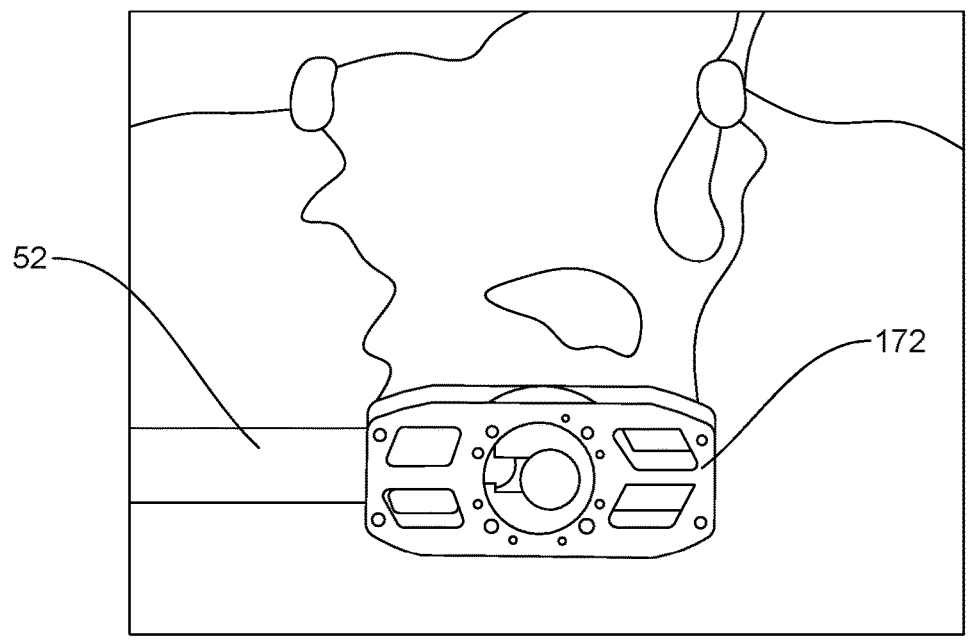
FIG. 27 is an eleventh graphical representation of a computer showing representations of the first and sixth components of the surgical system disposed with vertebrae.

In some embodiments, the software can generate one or more projections 172 that correspond to the polygonal or rectangular geometry an implant addition, such as, for example, one or more end plates of an implant, such as, for example, implant I, as shown in FIGS. 25 and 26. Projections 168, 170, 172 are saved, representing the cylindrical and rectangular geometries of implant I. Projections 168, 170, 172 are used to plan optimal placement and trajectory of implant I during actual implant insertion. It is envisioned that projections 172 can be used to provide representations of variously shaped and sized implant additions. In some embodiments, the software is configured to erase the resected vertebral body by moving template 52 within space S and removing the material from the visual representation of the patient's anatomy, as shown in FIG. 27. While the method disclosed above discusses using template 52 for estimation of implant size, position and trajectory, it is contemplated that template 54 and/or template 56 can be used in place of, or in addition to, template 52.

Figure 28:
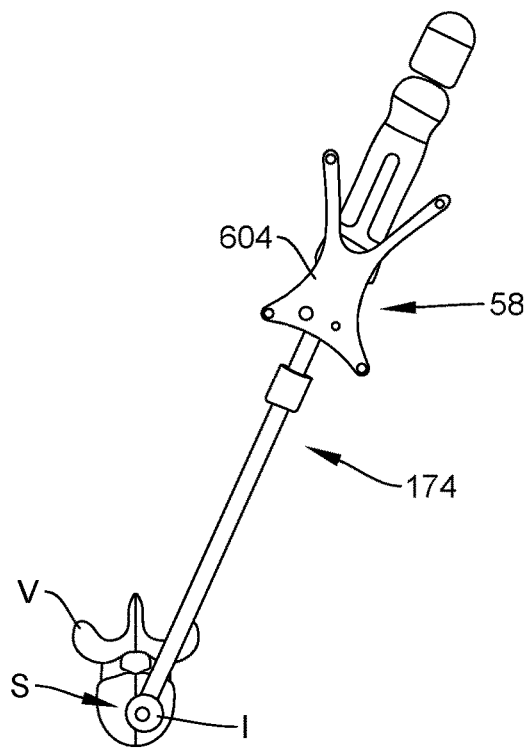
FIG. 28 is a first plan view of the sixth component and a seventh component of the surgical system disposed with vertebrae.
Figure 29:
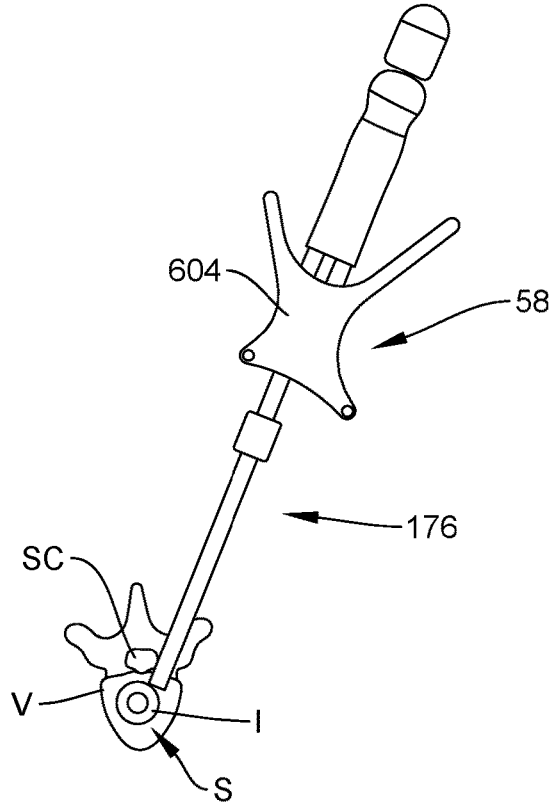
FIG. 29 is a first plan view of the sixth component and an eighth component of the surgical system disposed with vertebrae.

After the optimal implant size, position and trajectory is determined, an implant, such as, for example, implant I is selected from a plurality of implants having different sizes and/or geometries. In some embodiments, implant I is inserted into space S using a posterior approach. In some embodiments, an image guide, such as, for example, navigation component 58 is coupled to a surgical instrument, such as, for example, a straight inserter 174, as shown in FIG. 28. Implant I is coupled to inserter 174 and inserter 174 is manipulated to position implant I within space S using a posterior approach. In some embodiments, an image guide, such as, for example, navigation component 58 is coupled to a surgical instrument, such as, for example, an angled inserter 176, as shown in FIG. 29. Implant I is coupled to inserter 176 and inserter 176 is manipulated to position implant I within space S using a posterior approach, while facilitating ease of entry around spinal cord SC.

Figure 30:
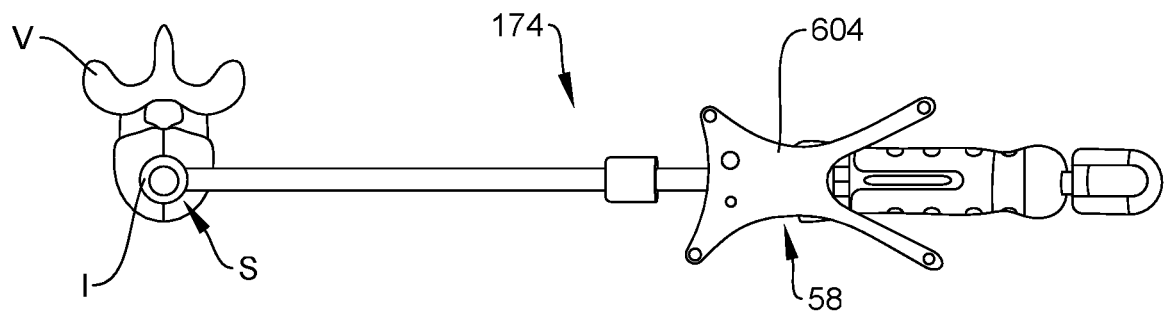
FIG. 30 is a second plan view of the sixth component and the seventh component of the surgical system disposed with vertebrae.

In some embodiments, implant I is inserted into space S using a lateral approach. For example, in some embodiments, an image guide, such as, for example, navigation component 58 is coupled to inserter 174 and inserter 174 is manipulated to position implant I within space S using a lateral approach, as shown in FIG. 30.

Figure 31:
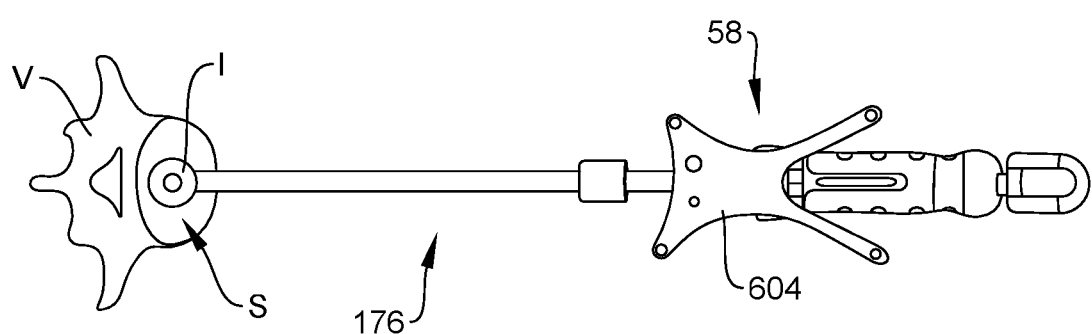
FIG. 31 is a second plan view of the fifth component and the eighth component of the surgical system disposed with vertebrae.
Figure 32:
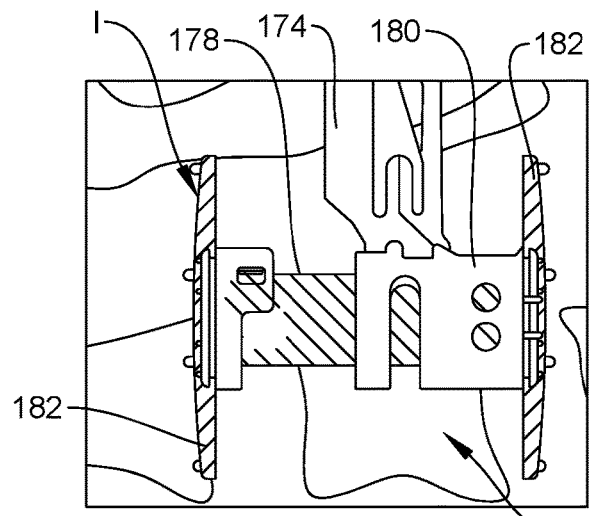
FIG. 32 is a first graphical representation of a computer showing representations of the sixth component and the seventh component of the surgical system disposed with vertebrae, with the sixth component in the expanded state.

In some embodiments, implant I is inserted into space S using an anterior approach. For example, in some embodiments, an image guide, such as, for example, navigation component 58 is coupled to inserter 174 and inserter 174 is manipulated to position implant I within space S using an anterior approach, as shown in FIG. 31.

Figure 33:
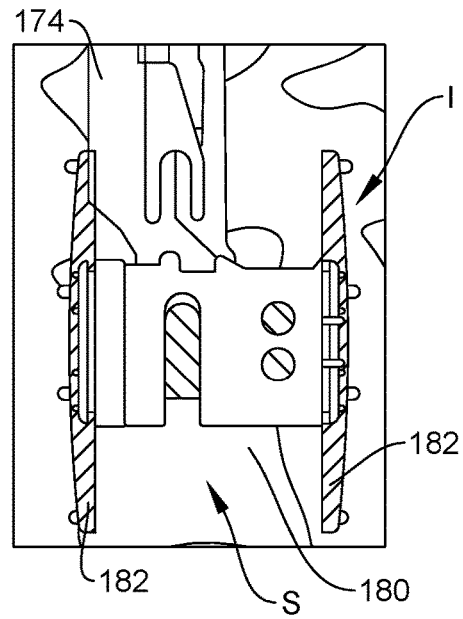
FIG. 33 is a second graphical representation of a computer showing representations of the sixth component and the seventh component of the surgical system disposed with vertebrae, with the sixth component in the collapsed state.
Figure 34:
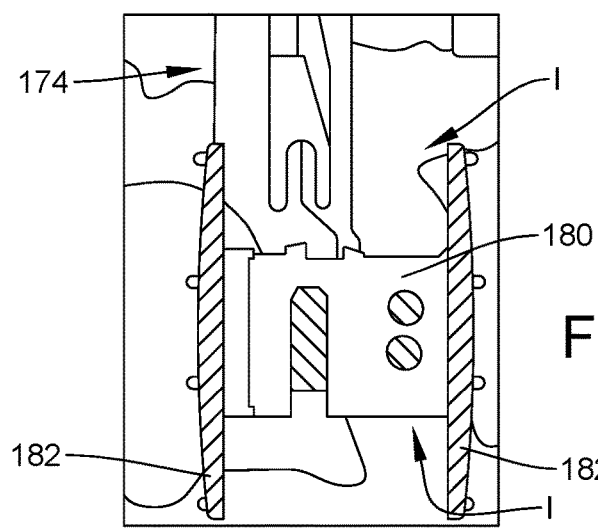
FIG. 34 is a third graphical representation of a computer showing representations of the sixth component and the seventh component of the surgical system disposed with vertebrae, with the sixth component in the collapsed state.
Figures 35, 36, 37:
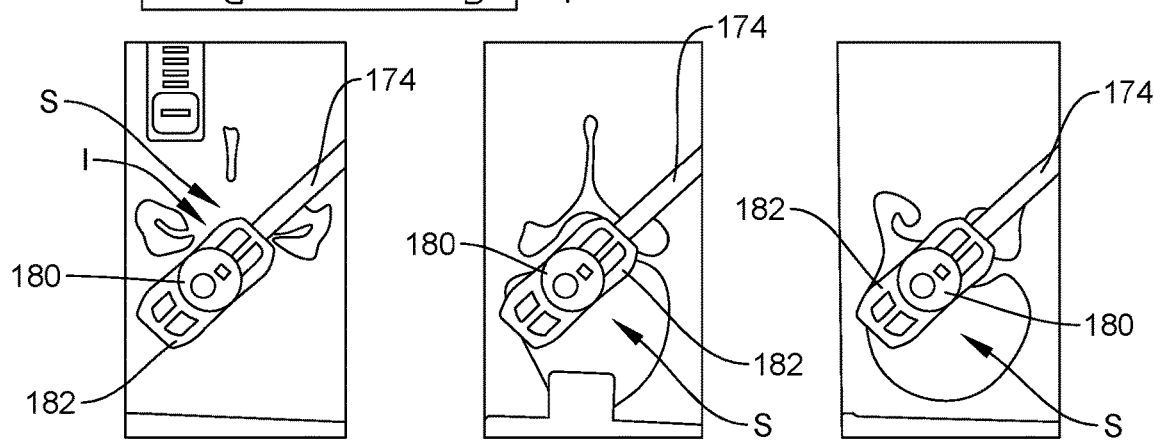
FIG. 35 is a fourth graphical representation of a computer showing representations of the sixth component and the seventh component of the surgical system disposed with vertebrae.
FIG. 36 is a fifth graphical representation of a computer showing representations of the sixth component and the seventh component of the surgical system disposed with vertebrae.
FIG. 37 is a sixth graphical representation of a computer showing representations of the sixth component and the seventh component of the surgical system disposed with vertebrae.
Figure 38:
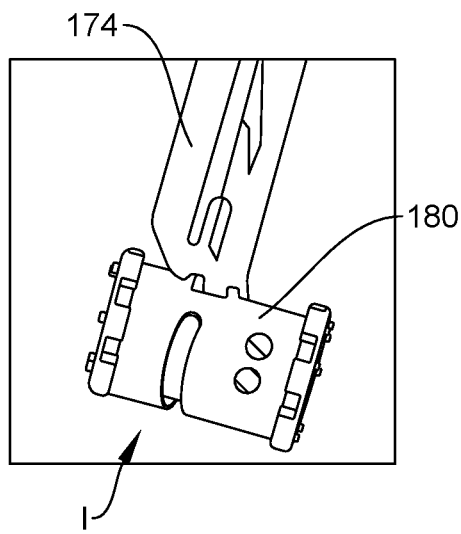
FIG. 38 is a seventh graphical representation of a computer showing representations of the sixth component and the seventh component of the surgical system disposed with vertebrae.
Figure 39:
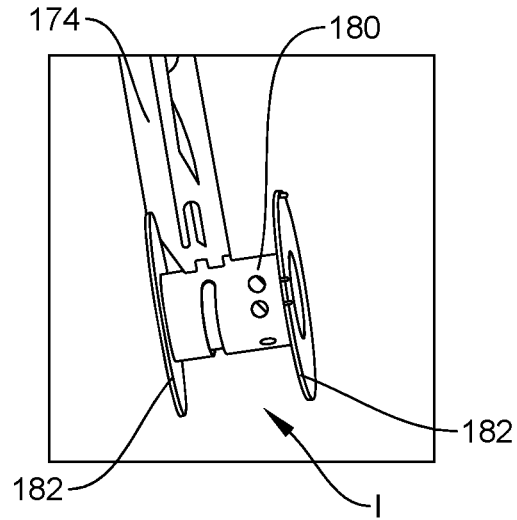
FIG. 39 is an eighth graphical representation of a computer showing representations of the sixth component and the seventh component of the surgical system disposed with vertebrae.
Figure 40:
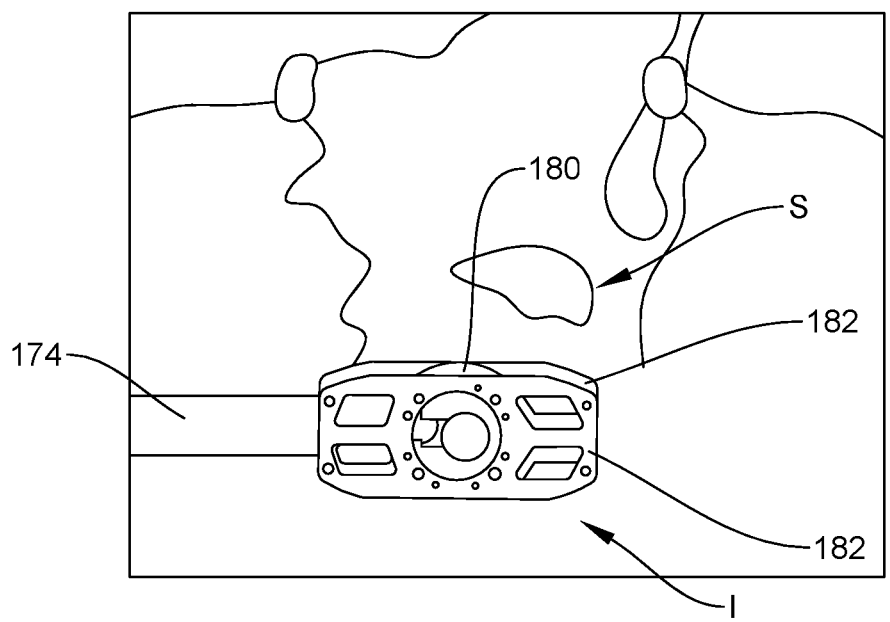
FIG. 40 is a ninth graphical representation of a computer showing representations of the sixth component and the seventh component of the surgical system disposed with vertebrae.

Navigation component 58 allows for visual representation of inserters 174, 176 in posterior, lateral and anterior approaches in multiple anatomical views of inserters 174, 176, implants and projections relative to the patient's anatomy. In some embodiments, computer 608 includes software configured to estimate appropriate final implant sizing, estimate appropriate implant placement and trajectory, and provide visualization of implant expansion. In some embodiments, the software provides visualization and distinction of implants and projections while estimating size, position, and trajectory with multiple implants and/or multiple implant additions in multiple states of representation. For example, in some embodiments, the software provides estimation of appropriate implant sizing through representations of an implant, such as, for example, implant I in the expanded state (FIG. 32) and the collapsed state (FIG. 33). In some embodiments, the intended direction of expansion of implant I is represented by a colored portion 178 that is a different color than a main body portion 180 of implant I. Implant additions, such as, for example, end plates 182 can be represented by a color that is different than the colors that represent portion 178 or portion 180, as shown in FIGS. 32-37. Geometries of varying color and/or transparency allow for easy visualization of anatomy while navigating. Varying transparency and coloration also provides a visual way to communicate to surgeons hardware components that are only being represented, but not navigated. In some embodiments, the software provides visualization of inserter 174, inserter 176, implant I and/or end plates 182 where multiple planes in a similar anatomical view are visible at once, as shown in FIGS. 35-37. This allows the surgeon to visualize where implant I is within space S. As shown in FIG. 38, implant I is shown without any implant additions, such as, for example, end plates 182. Implant I is then shown in FIG. 39 with end plates 182 attached. In some embodiments, the software is configured to allow for visualization of implant I in a lateral approach, as shown in FIG. 40, to ensure that end plates do not protrude out of the lateral annulus or lateral border of vertebra V, for example.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant template comprising:
a shaft extending along an axis between a proximal end and a distal end; and
an engagement portion configured for insertion to a surgical site of a patient, the engagement portion comprising a rod extending from the distal end at an acute angle relative to the axis and a head coupled to a distal end of the rod, the head being configured to facilitate entry of the engagement portion around a spinal cord of the patient and to the surgical site, the head being cylindrical and configured to remove bone and disc tissue between vertebrae, the head comprising a circular opening that extends through opposite superior and inferior surfaces of the head, the superior and inferior surfaces each extending parallel to the axis.

2. The spinal implant template recited in claim 1, wherein the acute angle is between about 1° and about 45°.

3. The spinal implant template recited in claim 1, wherein the acute angle is between about 20° and about 40°.

4. The spinal implant template recited in claim 1, wherein the head and the rod are monolithically formed with the shaft.

5. A surgical system comprising:
a spinal implant template comprising:
a shaft extending along an axis between a proximal end and a distal end, and
an engagement portion configured for insertion to a surgical site of a patient, the engagement portion comprising a rod extending from the distal end at an acute angle relative to the axis to facilitate entry of the engagement portion around a spinal cord of the patient and to the surgical site; and
an image guide attachable with the shaft, the image guide being positioned within a certain proximity of a sensor of a surgical navigation system such that the image guide communicates a signal representative of a position of the template to the sensor,
wherein the image guide includes an emitter configured to generate the signal representative of the position of the template, and
wherein the emitter includes opposite top and bottom surfaces, the emitter including fiducial markers extending from the top surface, the engagement portion comprising a head coupled to the rod, the head being cylindrical and defined by a wall that is circular in cross section, a top surface of the cylindrical wall being parallel with the top surface of the emitter.

6. The surgical system recited in claim 5, wherein the image guide includes an inner surface that defines a cavity configured for disposal of the shaft.

7. The surgical system recited in claim 5, wherein the image guide includes a lock engageable with a flange of the proximal end to fix the image guide with the template.

8. A surgical system comprising:
a first template comprising a first shaft extending along a first axis between a first proximal end and a first distal end, the first template comprising a first engagement portion configured for insertion between vertebrae of a patient, the first engagement portion comprising a first rod extending from the first distal end at an acute angle relative to the first axis and a first head coupled to the first rod, the first head being cylindrical and comprising a circular opening that extends through opposite superior and inferior surfaces of the first head, the circular opening extending perpendicular to the first axis, the first head having a first diameter; and
a second template comprising a second shaft extending along a second axis between a second proximal end and a second distal end, the second template comprising a second engagement portion configured for insertion between the vertebrae, the second engagement portion comprising a second rod extending from the second distal end at an acute angle relative to the second axis and a second head coupled to the second rod, the second head being cylindrical, the second head having a second diameter,
wherein the first diameter is different than the second diameter.

9. The surgical system recited in claim 8, further comprising an image guide attachable with the first shaft and the second shaft, the image guide being configured to be oriented relative to a sensor to communicate a signal representative of a position of the first template or a position of the second template.

10. The surgical system recited in claim 9, wherein the image guide includes an emitter configured to generate a signal representative of the position of the first template or the position of the second template.

11. The surgical system recited in claim 8, further comprising a third template comprising a third shaft extending along a third axis between a third proximal end and a third distal end, the third template comprising a third engagement portion configured for insertion between the vertebrae, the third engagement portion comprising a third rod extending from the third distal end such that the third rod is parallel to the third axis and a third head coupled to the third rod, the third head comprising a rectangular geometry.

12. The surgical system recited in claim 11, further comprising an image guide attachable with the first shaft, the second shaft and the third shaft, the image guide being configured to be oriented relative to a sensor to communicate a signal representative of a position of the first template, a position of the second template, or a position of the third template.

13. The surgical system recited in claim 12, wherein the image guide includes an emitter configured to generate a signal representative of the position of the first template, the position of the second template, or the position of the third template.

14. The surgical system recited in claim 8, further comprising an image guide attachable with the first shaft and oriented relative to a sensor to communicate a signal representative of a position of the first template, the image guide comprising a collar having a body and a pair of spaced apart tabs, the tabs each being deflectable relative to the body, the tabs each including an inner surface defining a cutout having a raised portion configured to receive a flange of first proximal end to connect the image guide with the first template.

15. A surgical system comprising:
a spinal implant template comprising:
a shaft extending along an axis between a proximal end and a distal end, the proximal end including a flange, and
an engagement portion configured for insertion between vertebrae of a patient, the engagement portion comprising a rod extending from the distal end at an acute angle relative to the axis to facilitate ease of entry around a spinal cord of the patient; and
an image guide attachable with the shaft and oriented relative to a sensor to communicate a signal representative of a position of the template, the image guide comprising a collar having a body and a pair of spaced apart tabs, the tabs each being deflectable relative to the body, the tabs each including an inner surface defining a cutout having a raised portion configured to receive the flange to connect the image guide with the template.

* * * * *